(12) United States Patent
Akuzawa

(10) Patent No.: US 10,480,973 B2
(45) Date of Patent: Nov. 19, 2019

(54) FLOW MEASURING DEVICE MEASURING AIR FLOW THROUGH A BYPASS PASSAGE THROTTLED BY A THROTTLE PORTION

(71) Applicant: DENSO CORPORATION, Kariya, Aichi-pref. (JP)

(72) Inventor: Hiroyuki Akuzawa, Kariya (JP)

(73) Assignee: DENSO CORPORATION, Kariya (JP)

( * ) Notice: Subject to any disclaimer, the term of this patent is extended or adjusted under 35 U.S.C. 154(b) by 190 days.

(21) Appl. No.: 15/665,721

(22) Filed: Aug. 1, 2017

(65) Prior Publication Data

US 2018/0038723 A1 Feb. 8, 2018

(30) Foreign Application Priority Data

Aug. 3, 2016 (JP) .................................. 2016-152808
Jul. 11, 2017 (JP) .................................. 2017-135655

(51) Int. Cl.
*G01M 15/04* (2006.01)
*G01F 1/684* (2006.01)
*F02D 9/10* (2006.01)
*G01F 1/69* (2006.01)
*F02M 35/10* (2006.01)
*F02D 41/18* (2006.01)
*F02D 9/02* (2006.01)
(Continued)

(52) U.S. Cl.
CPC ......... *G01F 1/6842* (2013.01); *F02D 9/1055* (2013.01); *F02D 41/187* (2013.01); *F02M 35/10386* (2013.01); *G01F 1/69* (2013.01); *F02D 2009/0294* (2013.01); *F02D 2400/18* (2013.01); *G01F 1/6845* (2013.01); *G01F 5/00* (2013.01); *G01M 15/048* (2013.01); *G01N 27/10* (2013.01)

(58) Field of Classification Search
USPC ............... 73/114.32, 114.33, 114.34, 114.35, 73/114.37
See application file for complete search history.

(56) References Cited

U.S. PATENT DOCUMENTS

| 2011/0023852 A1* | 2/2011 | Yamashita | ............. F01M 13/00 123/574 |
| 2012/0247202 A1* | 10/2012 | Kohno | ................... G01F 1/6842 73/204.25 |

(Continued)

FOREIGN PATENT DOCUMENTS

| JP | 2015-87196 | 5/2015 |
| WO | WO 2016/051940 | 4/2016 |

*Primary Examiner* — Eric S. McCall
(74) *Attorney, Agent, or Firm* — Nixon & Vanderhye PC

(57) ABSTRACT

A flow measuring device includes a housing including a bypass passage and a flow sensing chip located in the bypass passage and including a sensing surface portion. A throttle portion that is a part of a flowing passage wall facing a sensing surface portion throttles a cross-sectional area of a bypass passage. A position where the throttle portion starts is referred to as a start point position, and a position of the throttle portion where a distance between a gravity center of the sensing surface portion and the throttle portion is shortest is referred to as an end point position. The start point position and the end point position define an imagination line, and the imagination line and the flowing direction define an angle that is in a range from 0 degrees to 20 degrees.

11 Claims, 12 Drawing Sheets

(51) Int. Cl.
 *G01N 27/10* (2006.01)
 *G01F 5/00* (2006.01)

(56) References Cited

U.S. PATENT DOCUMENTS

| | | | |
|---|---|---|---|
| 2014/0331761 A1* | 11/2014 | Kaifu | F02M 35/10386 |
| | | | 73/204.25 |
| 2015/0168193 A1 | 6/2015 | Morino et al. | |
| 2017/0059381 A1* | 3/2017 | Ban | G01F 1/696 |
| 2017/0074703 A1* | 3/2017 | Tsuchiya | G01F 5/00 |

* cited by examiner

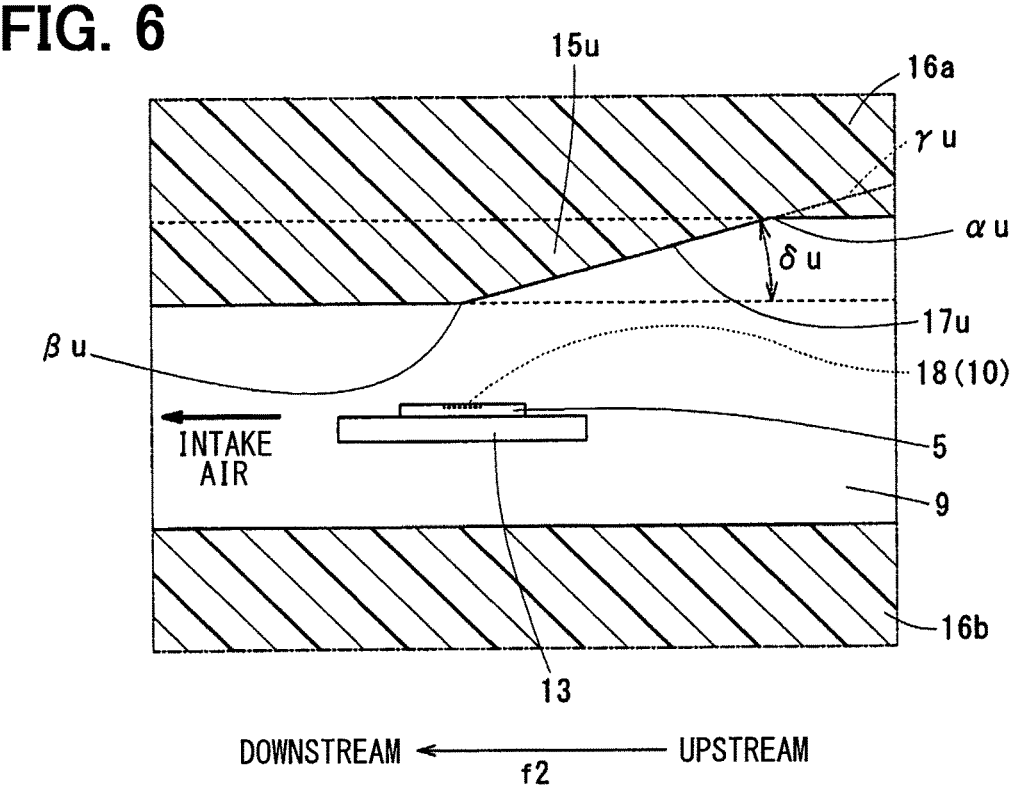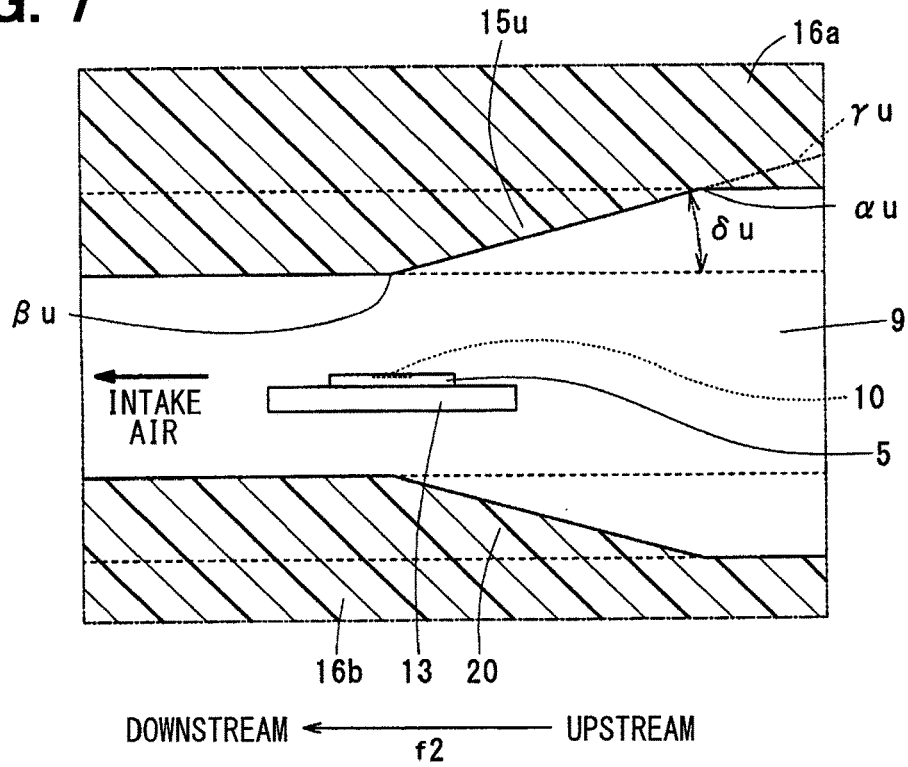

FLOW MEASURING DEVICE MEASURING AIR FLOW THROUGH A BYPASS PASSAGE THROTTLED BY A THROTTLE PORTION

CROSS REFERENCE TO RELATED APPLICATION

This application is based on Japanese Patent Application No. 2016-152808 filed on Aug. 3, 2016 and Japanese Patent Application No. 2017-135655 filed on Jul. 11, 2017, the disclosures of which are incorporated herein by reference.

TECHNICAL FIELD

The present disclosure relates to a flow measuring device that measures a flow volume of an intake air suctioned into an internal combustion engine used in a vehicle.

BACKGROUND

Conventionally, according to JP2014-001954A, it is known that a flowing measuring device includes a housing and a flow sensing chip. The housing includes a bypass passage introducing a part of an air flowing through an intake air channel of an internal combustion engine. The flow sensing chip is located in the bypass passage and includes a sensing surface portion generating an electrical signal in response to a flow volume of the air in the intake air channel by a heat transmission between the sensing surface portion and the air flowing through the bypass passage.

The sensing surface portion is located in a direction parallel to a flowing direction of a flow of the air flowing through the bypass passage. The bypass passage is throttled by a throttle portion such that a cross-sectional area of the bypass passage perpendicular to the flowing direction decreases in accordance with a decrease in distance from a gravity center of the sensing surface portion to a center of the cross-sectional area in the direction parallel to the flowing direction.

Thus, when the flow volume of the air in the intake air channel is relatively small, a flow rate of the air at the sensing surface portion can be sufficiently ensured, a heat transmission performance and a sensing accuracy of the flow volume can be ensured. However, when a flowing passage wall changes at the throttle portion at a sharp angle, a vortex or a separation is generated in the flow of the air in the vicinity of the throttle portion, and the flow of the air is disturbed to cancel a straightening function.

When the vortex is generated in the vicinity of the throttle portion, a flow of the air flowing in a reverse direction that is opposite to the flowing direction is generated. In this case, a pressure loss is generated in the bypass passage, and the flow volume at the sensing surface portion is decreased. Further, when the vortex is generated in the vicinity of the throttle portion in a case where the throttle portion is close to the sensing surface portion and a pulse flow is generated in response to an operation of a piston of the internal combustion engine, the vortex reaches the sensing surface portion to lead to a sensing error.

SUMMARY

It is an object of the present disclosure to provide a flow measuring device which includes a throttle portion and a sensing surface portion and improves a sensing accuracy of a flow volume at the sensing surface portion.

According to a first aspect of the present disclosure, the flowing measuring device includes a housing and a flow sensing chip. The housing includes a bypass passage that introduces a part of an air flowing through a duct. The flow sensing chip is located in the bypass passage and includes a sensing surface portion that generates an electrical signal in response to a flow volume of the air in the duct by a heat transmission between the sensing surface portion and the air flowing through the bypass passage.

The sensing surface portion is located along a flowing direction in which the air flows through the bypass passage. The bypass passage is throttled by a throttle portion such that a cross-sectional area of the bypass passage perpendicular to the flowing direction decreases in accordance with a decrease in distance from a gravity center of the sensing surface portion to a center of the cross-sectional area in a direction parallel to the flowing direction.

The throttle portion is a part of a flowing passage wall facing the sensing surface portion. The throttle portion throttles the cross-sectional area of the bypass passage such that a distance from the sensing surface portion to the flowing passage wall at the cross-sectional area in a direction perpendicular to the sensing surface portion decreases in accordance with a decrease in distance from the gravity center of the sensing surface portion to the center of the cross-sectional area in the direction parallel to the flowing direction. A position where the throttle portion starts is referred to as a start point position, and a position of the throttle portion where a distance between the gravity center of the sensing surface portion and the throttle portion is shortest is referred to as an end point position, the start point position and the end point position define an imagination line, and the imagination line and the flowing direction define an angle that is in a range from 0 degrees to 20 degrees.

Thus, since the flowing passage wall gradually varies in the throttle portion, it can be suppressed that a vortex or a separation is generated in the flow of the air in the vicinity of the throttle portion. Further, a disturb of the flow of the intake air generated by the throttle portion at the sensing surface portion can be suppressed. Furthermore, in the flow measuring device including the throttle portion, a sensing accuracy of the flow volume at the sensing surface portion can be improved.

According to a second aspect of the present disclosure, the flowing measuring device includes a housing and a flow sensing chip. The housing includes a bypass passage that introduces a part of an air flowing through a duct. The flow sensing chip is located in the bypass passage and includes a sensing portion that generates an electrical signal in response to a flow volume of the air in the duct. The bypass passage is throttled by a throttle portion such that a cross-sectional area of the bypass passage perpendicular to a flowing direction in which the air flows through the bypass passage decreases in accordance with a decrease in distance from a gravity center of the sensing surface portion to a center of the cross-sectional area in a direction parallel to the flowing direction.

The throttle portion is a part of a flowing passage wall facing the sensing surface portion. A position where the throttle portion starts is referred to as a start point position, and the start point position is located upstream of the sensing portion in the flowing direction. The throttle portion includes a surface that is a planar surface. The surface of the throttle portion and the flowing direction define an angle that is in a range from 0 degrees to 20 degrees.

Thus, similar to the first aspect, a disturb of the flow of the intake air generated by the throttle portion at the sensing surface portion can be suppressed. Further, in the flow measuring device including the throttle portion, a sensing accuracy of the flow volume at the sensing surface portion can be improved. In addition, the sensing portion may be a shape other than a planar shape.

According to a third aspect of the present disclosure, the flow measuring device includes a housing including a bypass passage that introduces a part of an air flowing through a duct, and a flow sensing chip located in the bypass passage and including a sensing surface portion that generates an electrical signal in response to a flow volume of the air in the duct by a heat transmission between the sensing surface portion and the air flowing through the bypass passage. The sensing surface portion is located along a flowing direction in which the air flows through the bypass passage. The bypass passage is throttled by a throttle portion such that a cross-sectional area of the bypass passage perpendicular to the flowing direction decreases in accordance with a decrease in distance from a gravity center of the sensing surface portion to a center of the cross-sectional area in a direction parallel to the flowing direction. The throttle portion is a part of a flowing passage wall that is included in the housing and faces the sensing surface portion, the throttle portion throttles the cross-sectional area of the bypass passage such that a distance from the sensing surface portion to the flowing passage wall at the cross-sectional area in a direction perpendicular to the sensing surface portion decreases in accordance with a decrease in distance from the gravity center of the sensing surface portion to the center of the cross-sectional area in the direction parallel to the flowing direction. A position where the throttle portion starts is referred to as a start point position, and a position of the throttle portion where a distance between the gravity center of the sensing surface portion and the throttle portion is shortest is referred to as an end point position. The start point position and the end point position define an imagination line, and the imagination line and the flowing direction define an angle that is in a range from 0 degrees to 30 degrees.

Thus, effects the same as that is the first aspect can be achieved.

According to a fourth aspect of the present disclosure, the flow measuring device includes a housing including a bypass passage that introduces a part of an air flowing through a duct, and a flow sensing chip located in the bypass passage and including a sensing portion that generates an electrical signal in response to a flow volume of the air in the duct. The bypass passage is throttled by a throttle portion such that a cross-sectional area of the bypass passage perpendicular to a flowing direction in which the air flows through the bypass passage decreases in accordance with a decrease in distance from a gravity center of the sensing surface portion to a center of the cross-sectional area in a direction parallel to the flowing direction. The throttle portion is a part of a flowing passage wall facing the sensing surface portion. A position where the throttle portion starts is referred to as a start point position, the start point position is located upstream of the sensing portion in the flowing direction. The throttle portion includes a surface that is a planar surface, the surface of the throttle portion and the flowing direction define an angle that is in a range from 0 degrees to 30 degrees.

Thus, effects the same as that is the first aspect can be achieved.

According to a fifth aspect of the present disclosure, the flow measuring device measures a flow volume of an air. The flow measuring device includes a bypass passage through which the air flows, a sensing portion outputting an electrical signal in response to the flow volume of the air in the bypass passage, a pair of flowing passage walls facing each other, the sensing portion located between the flowing passage walls, and a throttle portion throttling the bypass passage by protruding from the flowing passage walls toward the sensing portion, in an arrangement direction in which the pair of the flowing passage walls is arranged. The throttle portion has a protruding dimension gradually increases in accordance with a decrease in distance from the throttle portion to the sensing portion from an upstream end of the throttle portion in the bypass passage in a flowing direction in which the air flows through the bypass passage. A position of an upstream end of the throttle portion is referred to as a start point position, and a position of the throttle portion where a distance between the gravity center of the sensing surface portion and the throttle portion is shortest is referred to as an end point position. The start point position and the end point position define an imagination line, and the imagination line and the flowing direction define an angle that is in a range from 0 degrees to 30 degrees.

Thus, effects the same as that is the first aspect can be achieved.

BRIEF DESCRIPTION OF THE DRAWINGS

The above and other objects, features and advantages of the present disclosure will become more apparent from the following detailed description made with reference to the accompanying drawings. In the drawings:

FIG. 6 is a cross-sectional view showing the flow measuring device according to a second embodiment of the present disclosure and corresponding to FIG. 3 in the first embodiment;

FIG. 7 is a cross-sectional view showing the flow measuring device according to a third embodiment of the present disclosure and corresponding to FIG. 3 in the first embodiment;

DESCRIPTION OF EMBODIMENTS

Figure 1:
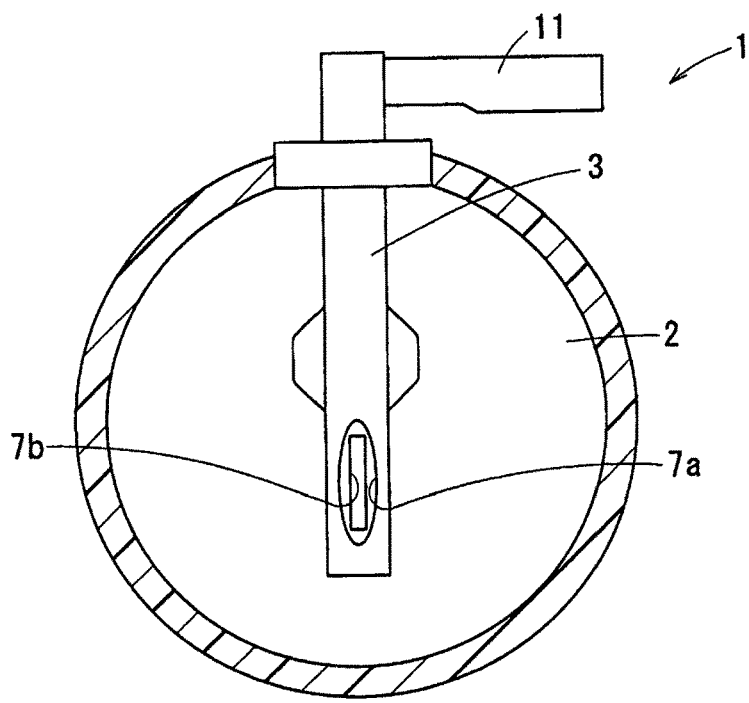
FIG. 1 is a diagram showing an outline of a flow measuring device viewed from an upstream of an intake air flow, according to a first embodiment of the present disclosure.

In the embodiments, a part that corresponds to a matter described in a preceding embodiment may be assigned with the same reference numeral, and redundant explanation for the part may be omitted. When only a part of a configuration is described in an embodiment, another preceding embodiment may be applied to the other parts of the configuration. The parts may be combined even if it is not explicitly described that the parts can be combined. The embodiments may be partially combined even if it is not explicitly described that the embodiments can be combined, provided there is no harm in the combination.

Hereafter, embodiments of the present disclosure will be described. In addition, the present disclosure is not limited to the embodiments that are examples of the present disclosure.

First Embodiment

Figure 2:
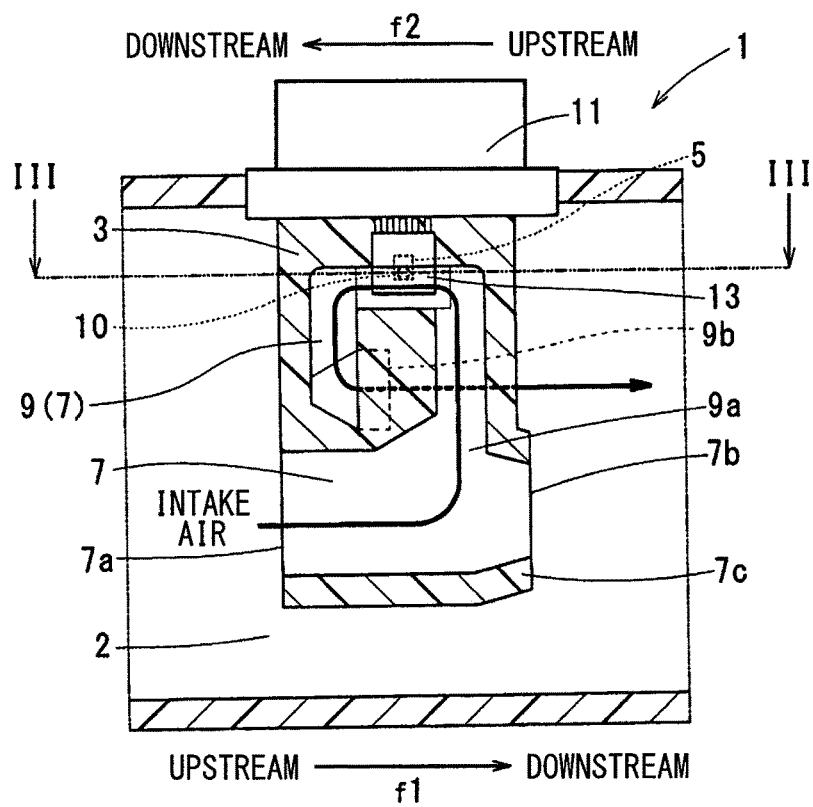
FIG. 2 is a cross-sectional view showing the flow measuring device along a flowing direction of an intake air, according to the first embodiment.
Figure 3:
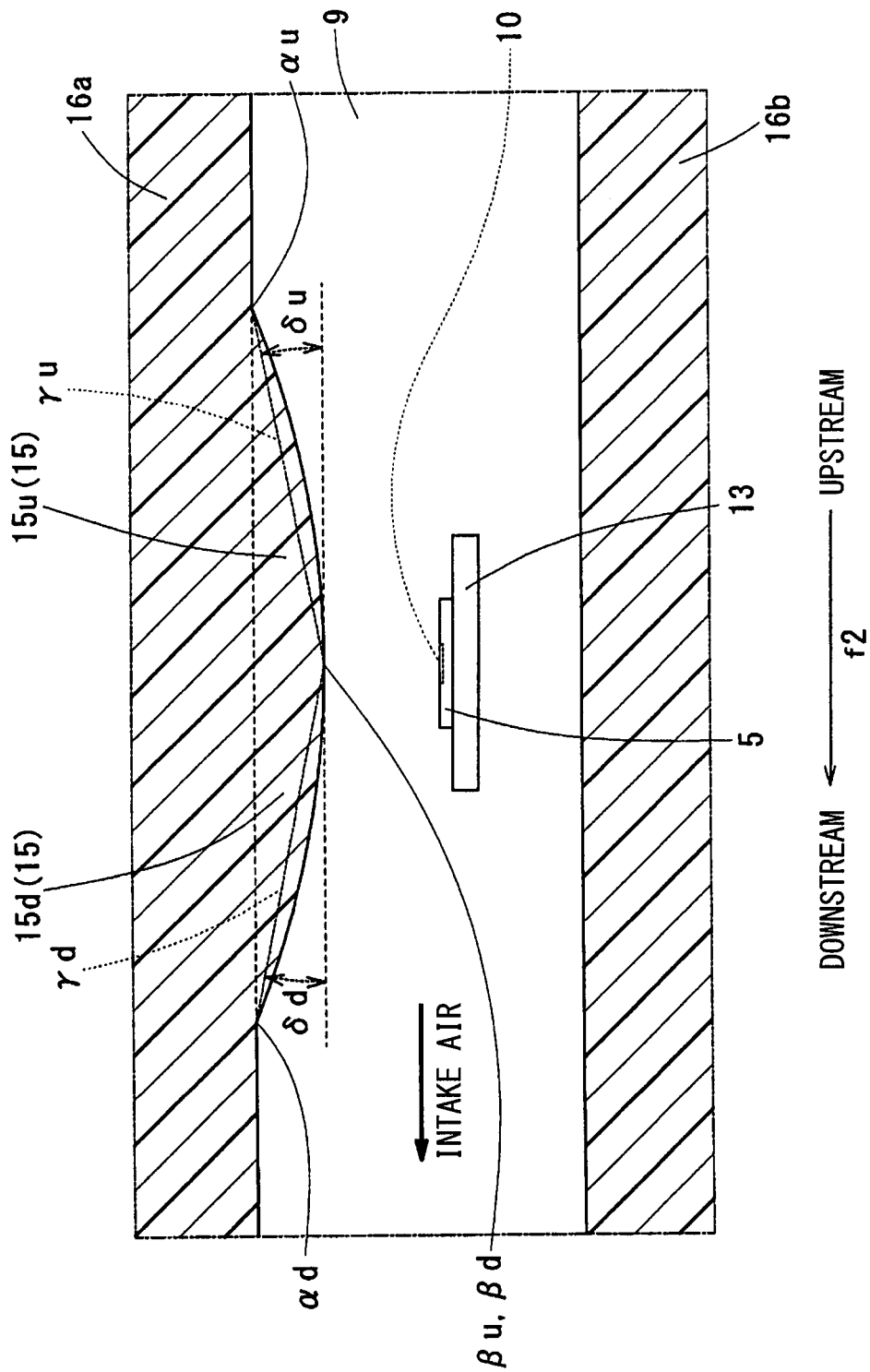
FIG. 3 is a cross-sectional view showing the flow measuring device and taken along a III-III line in FIG. 2, according to the first embodiment.

Referring to FIGS. 1 and 2, a flow measuring device 1 according to a first embodiment of the present disclosure will be described. The flow measuring device 1 is mounted to an intake air channel 2 that is a duct through which an intake air suctioned into an internal combustion engine used in a vehicle flows. The flow measuring device 1 measures a flow volume of the intake air flowing through the intake air channel 2. According to the present embodiment, a direction where the intake air in a center part of the intake air channel 2 flows is referred to as a first flowing direction f1. The center part of the intake air channel 2 is a part of the intake air channel 2 that is located at a center region of the intake air channel 2. A wall surface constituting the intake air channel 2 in the center part hardly affects a flow of the intake air. The flow measuring device 1 includes a housing 3, a flow sensing chip 5.

The housing 3 receives the flow sensing chip 5 and protrudes inwardly in a radial direction of the intake air channel 2 through which the intake air suctioned into the internal combustion engine flows. The housing 3 is made of a resin material and includes a bypass passage 7. The bypass passage 7 includes a sub-bypass passage 9 that branches off from the bypass passage 7.

The bypass passage 7 is a passage introducing a part of the intake air flowing through the intake air channel 2 and extends in a direction parallel to the first flowing direction f1. The bypass passage 7 includes a bypass inlet 7a located uppermost stream of the bypass passage 7 and a bypass outlet 7b located downmost stream of the bypass passage 7. The bypass passage 7 further includes an outlet throttle 7c located at a position adjacent to the bypass outlet 7b and throttling the flow of the intake air passing the bypass passage 7.

The sub-bypass passage 9 is a passage introducing a part of the intake air flowing through the bypass passage 7. The sub-bypass passage 9 includes a sub-bypass inlet 9a through which the part of the intake air flowing through the bypass passage 7 flows into and a sub-bypass outlet 9b through which the intake air flowing through the sub-bypass passage 9 is returned to the intake air channel 2. The sub-bypass passage 9 rotates the intake air flowing into the sub-bypass inlet 9a in the housing 3 and introduces the intake air to the sub-bypass outlet 9b. According to the present embodiment, the sub-bypass passage 9 extends from the sub-bypass inlet 9a in a direction different from the first flowing direction f1. Thus, a foreign matter such as a dust or an oil which is included in the intake air channel 2 and enters the bypass inlet 7a is separated to the bypass outlet 7b, and it can be suppressed that the foreign matter enters the sub-bypass passage 9.

The flow sensing chip 5 includes a sensing surface portion 10 located at a surface of the flow sensing chip 5. The sensing surface portion 10 senses the flow volume of the intake air. The sensing surface portion 10 is a planar shape. The sensing surface portion 10 is a heat transmission type and measures the flow volume by a heat transmission between the sensing surface portion 10 and the intake air passing the sub-bypass passage 9. The sensing surface portion 10 includes a heat generation resistor and a temperature sensing resistor that are located at a surface of the sensing surface portion 10.

The sensing surface portion 10 generates an electrical signal is response to the flow volume of the intake air of the sub-bypass passage 9. The flow sensing chip 5 outputs the electrical signal to an ECU that is not shown via a connection terminal in a connector 11. In other words, the flow sensing chip 5 indirectly outputs an electrical signal in response to the flow volume of the intake air in the intake air channel 2. According to the present embodiment, a direction where the intake air in a center part of the sub-bypass passage 9 flows is referred to as a second flowing direction f2. The center part of the sub-bypass passage 9 is a part of the sub-bypass passage 9 that is located at a center region of the sub-bypass passage 9. A wall surface of a flowing passage wall constituting the sub-bypass passage 9 in the center part hardly affects the flow of the intake air.

The flow sensing chip 5 is supported by a support portion 13, and the sensing surface portion 10 is exposed to the sub-bypass passage 9. Specifically, the flow sensing chip 5 is supported by the support portion 13 such that the surface of the sensing surface portion 10 is located in a direction parallel to the second flowing direction f2. The sensing surface portion 10 is located on a part of the surface of the flow sensing chip 5. According to the first embodiment, the first flowing direction f1 is opposite to the second flowing direction f2.

The sub-bypass passage 9 is throttled by a throttle portion 15 such that a cross-sectional area of the sub-bypass passage 9 perpendicular to the second flowing direction f2 decreases in accordance with a decrease in distance from a gravity center of the sensing surface portion 10 to a center of the cross-sectional area in the direction parallel to the second flowing direction f2. The throttle portion 15 is a part of a first flowing passage wall 16a constituting the sub-bypass passage 9 and faces the sensing surface portion 10. A second flowing passage wall 16b constituting the sub-bypass passage 9 is opposite to the first flowing passage wall 16a. In other words, the flow sensing chip 5 is supported between a pair of flowing passage walls that is the first flowing passage wall 16a and the second flowing passage wall 16b by the support portion 13. According to the present embodiment, the housing 3 includes the first flowing passage wall 16a and the second flowing passage wall 16b.

The throttle portion 15 throttles the cross-sectional area of the sub-bypass passage 9 such that a distance from the sensing surface portion 10 to the first flowing passage wall 16a at the cross-sectional area in a direction perpendicular to the sensing surface portion 10 decreases in accordance with a decrease in distance from the gravity center of the sensing surface portion 10 to the center of the cross-sectional area in the direction parallel to the second flowing direction f2. The throttle portion 15 extends in the direction parallel to the second flowing direction f2. The throttle portion 15 includes a first throttle portion 15u located upstream of the gravity center of the sensing surface portion 10 in the second flowing direction f2 and a second throttle portion 15d located downstream of the gravity center of the sensing surface portion 10 in the second flowing direction f2. The throttle portion 15 is a shape elongated in the direction parallel to the second flowing direction f2.

A position where the first throttle portion 15u starts is referred to as a first start point position αu, and a position of the first throttle portion 15u where a distance between the gravity center of the sensing surface portion 10 and the first throttle portion 15u is shortest is referred to as a first end point position βu. In this case, the distance is referred to as a shortest distance between the gravity center of the sensing surface portion 10 and the first throttle portion 15u. The first start point position αu and the first end point position βu define a first imagination line γu. The first imagination line γu and the second flowing direction f2 define a first angle δu that is in a range from 0 degrees to 20 degrees.

The first start point position αu is located uppermost stream of the first throttle portion 15u in the second flowing direction f2. According to the present embodiment, at the position where the distance between the first throttle portion 15u and the gravity center of the sensing surface portion 10 is shortest, a total distance that is a sum of a distance between the gravity center of the sensing surface portion 10 and the first flowing passage wall 16a at the first throttle portion 15u in the direction perpendicular to the sensing surface portion 10 and a distance between the gravity center of the sensing surface portion 10 and the first flowing passage wall 16a at the first throttle portion 15u in the direction parallel to the second flowing direction f2 becomes shortest. In this case, the total distance is equivalent to the shortest distance between the gravity center of the sensing surface portion 10 and the first throttle portion 15u.

When plural start point positions αu exist, the first start point position αu is a position where a distance between the first start point position αu and the first end point position βu is shortest. In this case, the distance is referred to as a shortest distance between the first start point position αu and the first end point position βu. According to the present embodiment, at the position where the distance between the first start point position αu and the first end point position βu is shortest, a total distance that is a sum of a distance between the first start point position αu and the first end point position βu in the direction perpendicular to the sensing surface portion 10 and a distance between the first start point position αu and the first end point position βu in the direction parallel to the second flowing direction f2 becomes shortest. In this case, the total distance is equivalent to the shortest distance between the first start point position αu and the first end point position βu.

A position where the second throttle portion 15d starts is referred to as a second start point position αd, and a position of the second throttle portion 15d where a distance between the gravity center of the sensing surface portion 10 and the second throttle portion 15d is shortest is referred to as a second end point position βd. In this case, the distance is referred to as a shortest distance between the gravity center of the sensing surface portion 10 and the second throttle portion 15d. The second start point position αd and the second end point position βd define a second imagination line γd. The second imagination line γd and the second flowing direction f2 define a second angle δd that is in a range from 0 degrees to 20 degrees. According to the present embodiment, the second flowing direction f2 is parallel to the sensing surface portion 10. The second start point position αd is located lowermost stream of the second throttle portion 15d in the second flowing direction f2.

The first throttle portion 15u and the second throttle portion 15d have surfaces that are curved surfaces protruding inwardly in a radial direction of the sub-bypass passage 9. Specifically, the throttle portion 15 including the first throttle portion 15u and the second throttle portion 15d includes a side surface facing the sensing surface portion 10. In this case, the side surface is also a side surface of a cylinder having an axis extending in a height direction that is perpendicular to the second flowing direction f2 and is parallel to the sensing surface portion 10.

According to the present embodiment, in the flow measuring device 1, the sub-bypass passage 9 is throttled by the first throttle portion 15u such that the cross-sectional area of the sub-bypass passage 9 perpendicular to the second flowing direction f2 decreases in accordance with a decrease in distance from the gravity center of the sensing surface portion 10 to the center of the cross-sectional area in the direction parallel to the second flowing direction f2. The first throttle portion 15u is a part of the first flowing passage wall 16a and faces the sensing surface portion 10. The first throttle portion 15u throttles the cross-sectional area of the sub-bypass passage 9 such that the distance from the sensing surface portion 10 to the first flowing passage wall 16a at the cross-sectional area in the direction perpendicular to the sensing surface portion 10 decreases in accordance with a decrease in distance from the gravity center of the sensing surface portion 10 to the center of the cross-sectional area in the direction parallel to the second flowing direction f2.

Since the first start point position αu is a position where the first throttle portion 15u starts and the first end point position βu is the position of the first throttle portion 15u where the distance between the gravity center of the sensing surface portion 10 and the first throttle portion 15u is shortest, the first angle δu defined by the first imagination line γu and the second flowing direction f2 is in a range from 0 degrees to 20 degrees.

Thus, since the first flowing passage wall 16a gradually varies in the first throttle portion 15u, it can be suppressed that a vortex or a separation is generated in the flow of the intake air in the vicinity of the first throttle portion 15u. Further, a disturb of the flow of the intake air generated by the first throttle portion 15u at the sensing surface portion 10 can be suppressed. Furthermore, in the flow measuring device 1 including the first throttle portion 15u, a sensing accuracy of the flow volume at the sensing surface portion 10 can be improved.

The surface of the first throttle portion 15u is a curved surface protruding inwardly in the radial direction of the sub-bypass passage 9. Thus, a variation relative to a flowing direction of the surface of the first throttle portion 15u can be maintained to be smooth, and the cross-sectional area of the sub-bypass passage 9 perpendicular to the second flowing direction f2 can be decreased. Further, it can be suppressed that the vortex or the separation is generated in the flow of the intake air in the vicinity of the first throttle portion 15u, and it can be reduced that a pressure loss is generated in the sub-bypass passage 9.

The first throttle portion 15u and the second throttle portion 15d are located upstream and downstream of the sensing surface portion 10 in the second flowing direction f2, respectively. Since the second throttle portion 15d is located downstream of the sensing surface portion 10 in the second flowing direction f2, the flow measuring device 1 can properly measure the flow volume in a case where a pulse flow is generated in response to an operation of a piston of the internal combustion engine. In other words, when a flow of a gas flowing from downstream to upstream, a flow rate at the sensing surface portion 10 can be ensured, and the flow measuring device 1 can properly measure the flow volume.

Figure 4:
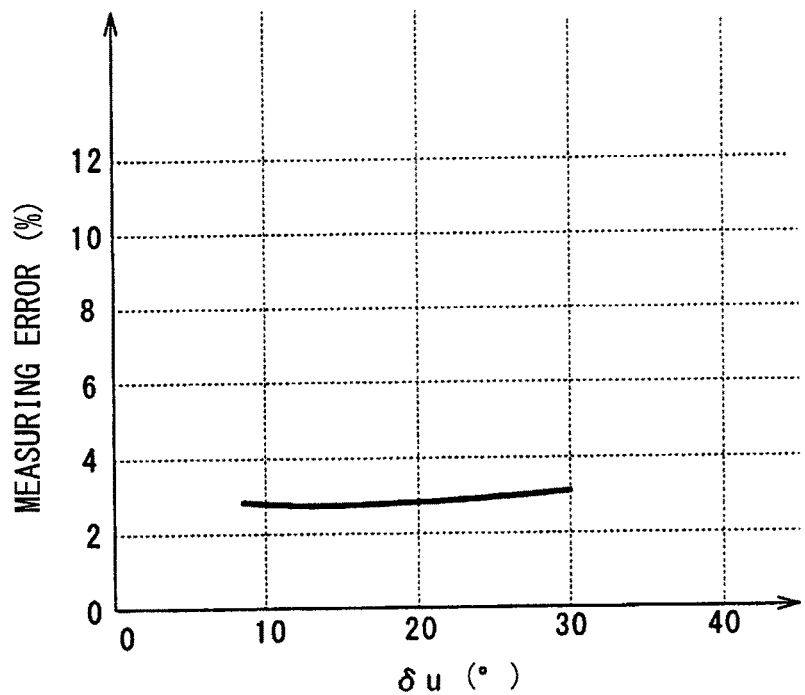
FIG. 4 is a graph showing a relationship between a measuring error and an angle in a case where a vibration frequency is 100 Hz, according to the first embodiment.
Figure 5:
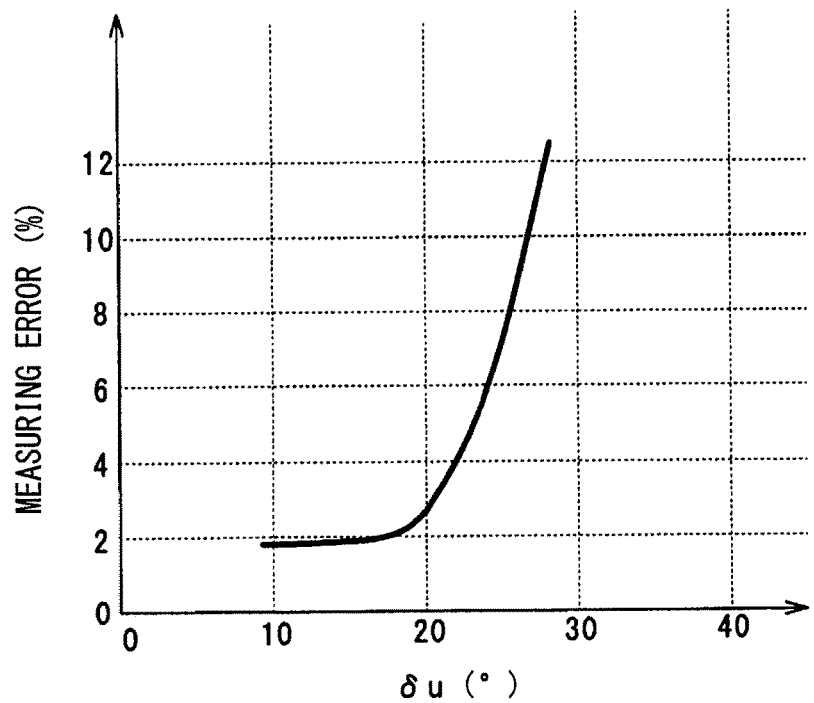
FIG. 5 is a graph showing a relationship between the measuring error and the angle in a case where the vibration frequency is 130 Hz, according to the first embodiment.

FIGS. 4 and 5 are graphs plotting measuring errors of when the first angle δu is changed. As shown in FIG. 4, when a vibration frequency of the flow volume is low, the measuring error is relatively small without respect to a value of the first angle δu, and the flow measuring device 1 has a characteristic that changes in response to a change of the flow volume. In the change of the flow volume, the flow volume increases or decreases. As shown in FIG. 5, when the vibration frequency of the flow volume is high, the measuring error increases in a case where the first angle δu exceeds 20 degrees, and the characteristic is deteriorated. Since the vibration frequency increases, the vortex or the separation is readily generated in the flow of the intake air, and a level of an influence of the first angle δu on the measuring error becomes higher. According to the present embodiment, the vibration frequency of the flow volume is equivalent to a vibration frequency of the pulse flow generated in response to the operation of the piston of the internal combustion engine. The vibration frequency of the flow volume has a predetermined value as a central value, and indicates a frequency of when the flow volume changes at a predetermined vibration amplitude.

Second Embodiment

Referring to FIG. 6, components of the flow measuring device 1 according to a second embodiment of the present disclosure that are different from that according to the first embodiment will be described. In addition, the substantially same parts and the components as the embodiments of the present disclosure are indicated with the same reference numeral. According to the present embodiment, in the flow measuring device 1, the first throttle portion 15u includes a surface 17u that is a planar surface. Further, according to the present embodiment, the second throttle portion 15d is cancelled. Thus, according to the present embodiment, the first throttle portion 15u is referred to as a throttle portion 15u.

FIG. 6 indicates a start point position αu, an end point position βu, an imagination line γu and an angle δu that are equivalent to the first start point position αu, the first end point position βu, the first imagination line γu and the first angle δu of the first embodiment. Specifically, the start point position αu is located upstream of the sensing surface portion 10 that is a sensing portion 18 in a flowing direction f2 that is equivalent to the second flowing direction f2 of the first embodiment. The surface 17u of the throttle portion 15u and the flowing direction f2 define an angle that is equal to the angle δu.

Thus, a variation relative to a flowing direction of the surface of the throttle portion 15u can be maintained to be smooth, the cross-sectional area of the sub-bypass passage 9 perpendicular to the flowing direction f2 can be decreased at the sensing portion 18, and the flow rate at the sensing portion 18 can be ensured. Since the cross-sectional area gradually varies, a variation amount of the flow rate generated by the throttle portion 15u in the vicinity of the surface 17u is small, it can be suppressed that a vortex is generated. Since the surface 17u is a planar surface, it is difficult that a flow rate variation in a direction perpendicular to a flow flowing in a direction along the surface 17u is generated, and it can be suppressed that the separation is generated. In addition, since the surface 17u is a planar surface, the surface 17u is readily to be formed.

Third Embodiment

Referring to FIG. 7, components of the flow measuring device 1 according to a third embodiment of the present disclosure that are different from that according to the second embodiment will be described. According to the present embodiment, in the flow measuring device 1, a second throttle portion 20 that is different from the first throttle portion 15u is located on the second flowing passage wall 16b. Since at least two throttle portions are provided in the sub-bypass passage 9, the cross-sectional area of the sub-bypass passage 9 can be further decreased when the angle δu is maintained to be smaller than 20 degrees. Then, the flow rate of the intake air at the sensing surface portion 10 can be further increased, and a heat transmission performance and the sensing accuracy can be further stabilized.

When the first throttle portion 15u is provided at the first flowing passage wall 16a and the vortex directly reaches the sensing surface portion 10, the influence of the vortex on the flow of the intake air at the sensing surface portion 10 becomes maximum. Then, it is unlikely that the vortex generated due to the throttle portion located at a flowing passage wall other than the first flowing passage wall 16a reaches the sensing surface portion 10, and the influence of the vortex on the flow of the intake air at the sensing surface portion 10 decreases. Thus, the second throttle portion 20 located on the second flowing passage wall 16b does not affect the flow of the intake air at the sensing surface portion 10, and the second throttle portion 20 can adjust the cross-sectional area of the sub-bypass passage 9.

Fourth Embodiment

According to the first embodiment, when the vibration frequency of the flow volume is high and the first angle δu exceeds 20 degrees, the measuring error increases. According to a fourth embodiment of the present disclosure, when the vibration frequency of the flow volume is high and the first angle δu is 30 degrees, the measuring error is still relatively small. According to the present embodiment, components of the flow measuring device 1 that are different from that according to the first embodiment will be described.

Figure 8:
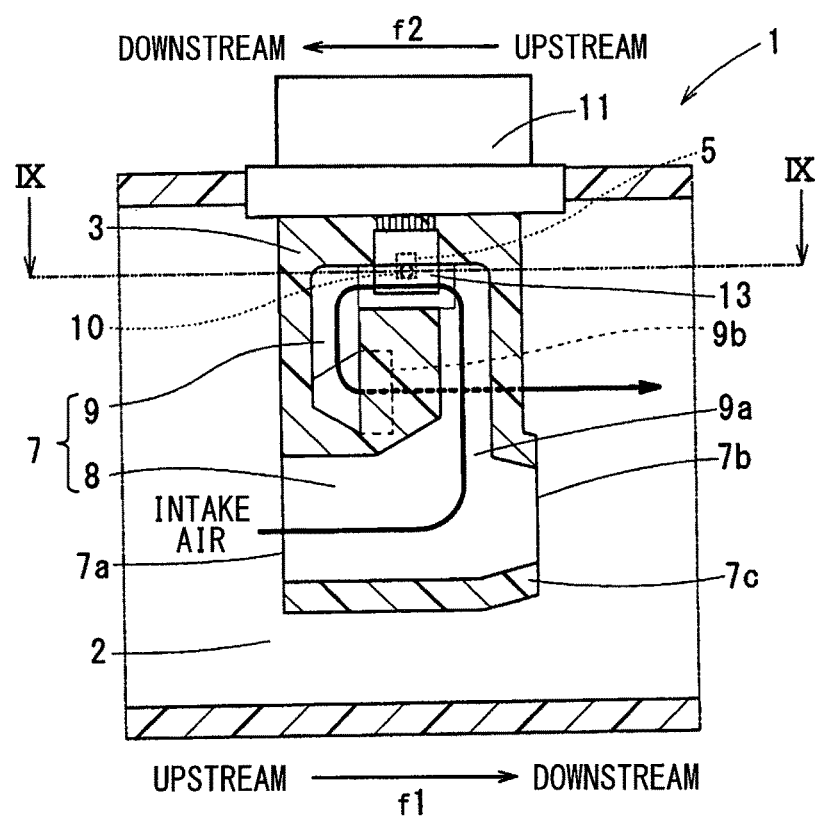
FIG. 8 is a cross-sectional view showing the flow measuring device according to a fourth embodiment of the present disclosure and corresponding to FIG. 2 in the first embodiment.

According to the present embodiment, as shown in FIG. 8, a part of the bypass passage 7 from the bypass inlet 7a to the bypass outlet 7b is referred to as a passing passage 8. The passing passage 8 includes an upstream end portion where the bypass inlet 7a is located and a downstream end portion where the bypass outlet 7b is located. The passing passage 8 extends in the direction parallel to the first flowing direction f1 of the intake air channel 2. According to the present embodiment, the sub-bypass passage 9 can be referred to as a branch passage that branches off from an intermediate part of the passing passage 8.

Figure 9:
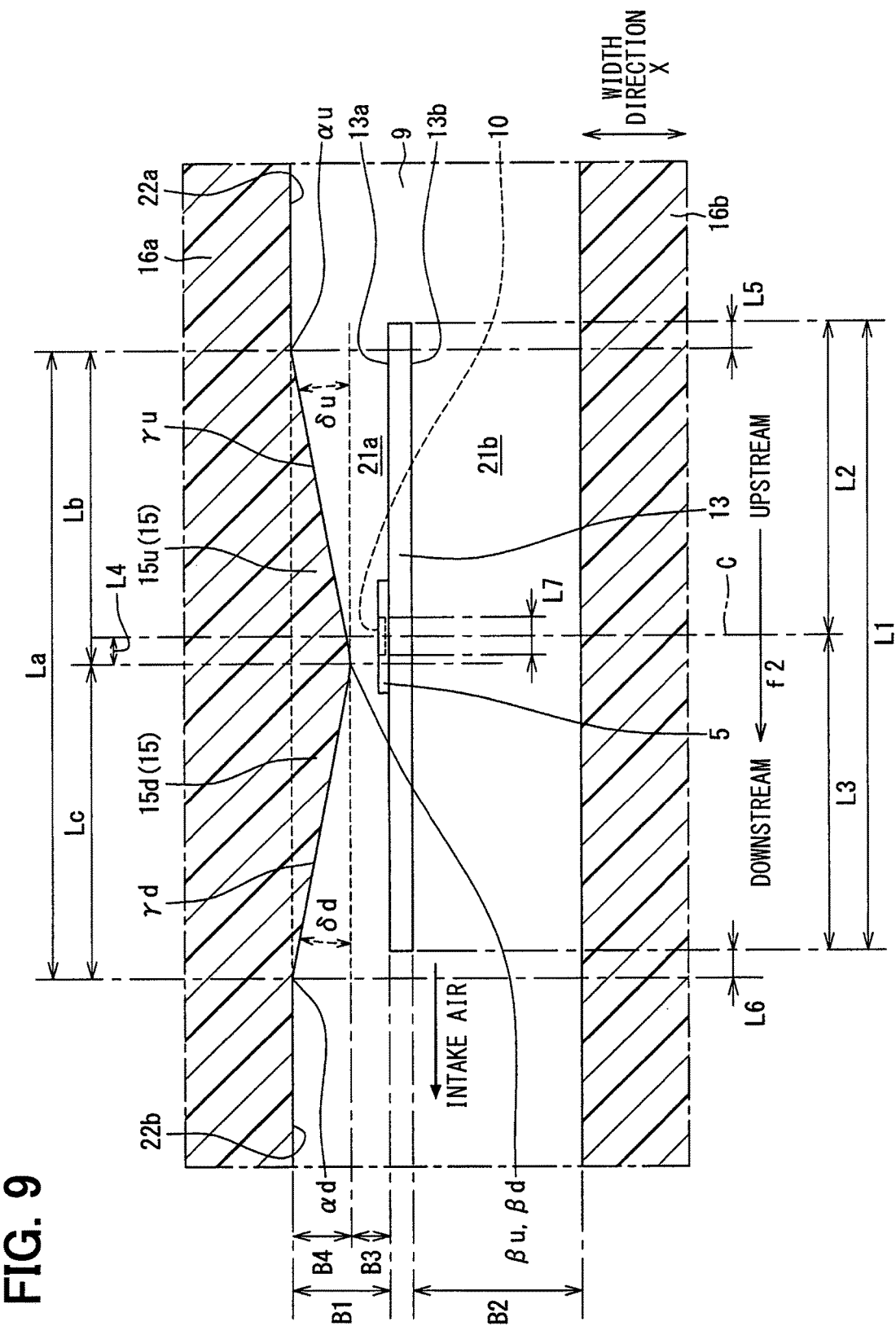
FIG. 9 is a cross-sectional view showing the flow measuring device and taken along a IX-IX line in FIG. 8, according to the fourth embodiment.

According to the present embodiment, as shown in FIG. 9, the first throttle portion 15u includes an inner peripheral surface straightly extending from the first start point position αu to the first end point position αd, and the second throttle portion 15d includes an inner peripheral surface straightly extending from the second start point position βu to the second end point position βd. According to the present embodiment, the inner peripheral surface of the first throttle portion 15u is equivalent to a surface of the first throttle portion 15u according to the first embodiment. According to the present disclosure, the first throttle portion 15u and the second throttle portion 15d include inner peripheral surfaces that may be have a part that is recessed or protruded or curved, respectively. The first angle δu and the second angle δd are equal to 30 degrees. The first throttle portion 15u is equivalent to an upstream throttle portion. The sensing surface portion 10 is referred to as a sensing portion.

A pair of flowing passage walls including the first flowing passage wall 16a and the second flowing passage wall 16b is arranged in an arrangement direction that is referred to as a width direction X. The first flowing passage wall 16a includes the first throttle portion 15u and the second throttle portion 15d, and the second flowing passage wall 16b excludes the first throttle portion 15u and the second throttle portion 15d. The width direction X is an orthogonal direction that is perpendicular to the second flowing direction f2. The support portion 13 is made of a synthetic resin material and is a plate shape. The support portion 13 divides the sub-bypass passage 9 into two regions in the width direction. The support portion 13 is located to be parallel to the first flowing passage wall 16a and the second flowing passage wall 16b and extends in the direction parallel to the second flowing direction f2. The support portion 13 is also located to be parallel to a direction in which the first start point position αu and the second start point position αd are arranged. The support portion 13 includes a first opposite surface 13a facing the first flowing passage wall 16a and a second opposite surface 13b facing the second flowing passage wall 16b. The flow sensing chip 5 and the sensing surface portion 10 are located on the first opposite surface 13a.

The support portion 13 has a support length L1 that is a length of the support portion 13 in the direction parallel to the second flowing direction f2 that is equal to a throttle length La that is a total length of the first throttle portion 15u and the second throttle portion 15d in the direction parallel to the second flowing direction f2. The flow sensing chip 5 and the sensing surface portion 10 are located at a center of the support portion 13 in the direction parallel to the second flowing direction f2. In other words, the flow sensing chip 5 and the sensing surface portion 10 are located such that center lines of the flow sensing chip 5 and the sensing surface portion 10 that are parallel to the width direction X match a center line C of the support portion 13 that is perpendicular to the second flowing direction f2. A first support distance L2 that is a distance from an upstream end of the support portion 13 to the center line C is equal to a second support distance L3 that is a distance from the center line C to a downstream end of the support portion 13.

The center line C of the support portion 13 is located at a position upstream of the first end point position βu and the second end point position βd in the second flowing direction f2. The upstream end of the support portion 13 is located upstream of the first start point position αu in the second flowing direction f2, and the downstream end of the support portion 13 is located upstream of the second start point position αd in the second flowing direction f2. The center line C, the first end point position βu and the second end point position βd define a distance in the direction parallel to the second flowing direction f2 that is referred to as a center shift distance L4. The upstream end of the support portion 13 and the first start point position αu define a distance that is referred to as an upstream shift distance L5. The downstream end of the support portion 13 and the second start point position αd define a distance that is referred to as a downstream shift distance L6. Since the support length L1 of the support portion 13 is equal to the throttle length La of the first throttle portion 15u and the second throttle portion 15d, the center shift distance L4, the upstream shift distance L5 and the downstream shift distance L6 are equal to each other.

The throttle length La is also a distance from the first start point position αu to the second start point position αd. The first throttle portion 15u located upstream of the gravity center of the sensing surface portion 10 has a length in the direction parallel to the second flowing direction f2 that is referred to as a first throttle length Lb and is equal to a length of the second throttle portion 15d located downstream of the gravity center of the sensing surface portion 10 in the direction parallel to the second flowing direction f2 that is referred to as a second throttle length Lc. The throttle length La is a sum of the first throttle length Lb and the second throttle length Lc. In this case, the first angle δu is equal to the second angle δd, and the first end point position βu and the second end point position βd are located at a center between the first start point position αu and the second start point position αd.

The sensing surface portion 10 is located between the first start point position αu and the first end point position βu or between the first start point position αu and the second end point position βd in the direction parallel to the second flowing direction f2. The sensing surface portion 10 is located at a position close to the first end point position βu and the second end point position βd, and the sensing surface portion 10 does not protrude to a position downstream of the first end point position βu and the second end point position βd in the second flowing direction f2. The sensing surface portion 10 is located to be close to the first end point position βu and the second end point position βd such that the flow sensing chip 5 protrudes to a position downstream of the first end point position βu and the second end point position βd in the second flowing direction f2. In a configuration that the sensing surface portion 10 does not protrude to a position downstream of the first end point position βu and the second end point position βd in the second flowing direction f2, a half of a sensing length L7 that is a length of the sensing surface portion 10 in the direction parallel to the second flowing direction f2 is shorter than the center shift distance L4. In this case, a center part of the sensing surface portion 10 is located upstream of the first end point position βu and the second end point position βd.

The support portion 13 is located at a position where the first flowing passage wall 16a is closer to the support portion 13 than the second flowing passage wall 16b is in the width direction X. A first facing distance B1 that is a distance from the first start point position αu and the second start point position αd to the support portion 13 in the width direction X is shorter than a second facing distance B2 that is a distance from the support portion 13 to the second flowing passage wall 16b in the width direction X. A gap distance B3 that is a distance from the first end point position βu and the second end point position βd to the support portion 13 in the width direction X is shorter than a throttle distance B4 that is a distance from the first start point position αu and the second start point position αd to the first end point position βu and the second end point position βd in the width direction X. The first facing distance B1 is a sum of the gap distance B3 and the throttle distance B4. The gap distance B3 is longer than a thickness of the support portion 13 and a thickness of the flow sensing chip 5.

A space between the first flowing passage wall 16a and the support portion 13 is referred to as a first region 21a where the sensing surface portion 10 is located, and a space between the support portion 13 and the second flowing passage wall 16b is referred to as a second region 21b. According to the present embodiment, the first region 21a is equivalent to a sensing region, and the second region 21b is equivalent to an opposite region. The support portion 13 is located between the sensing surface portion 10 and the second region 21b. A width of the first region 21a in the width direction X gradually decreases from the first start point position αu to the first end point position βu in the second flowing direction f2 and gradually increases from the second end point position βd to the second start point position αd in the second flowing direction f2.

The first flowing passage wall 16a further includes an upstream wall surface 22a that is a wall surface located upstream of the first start point position αu and a downstream wall surface 22b that is a wall surface located downstream of the second start point position αd. Thus, the first region 21a is also defined by the upstream wall surface 22a and the support portion 13. The upstream wall surface 22a and the downstream wall surface 22b are in contact with the first start point position αu and the second start point position αd, respectively. A distance from the upstream wall surface 22a and the downstream wall surface 22b to the support portion 13 in the width direction X is equal to the first facing distance B1.

According to the present embodiment, since the inner peripheral surfaces of the first throttle portion 15u and the second throttle portion 15d extends straightly, the first angle δu is equal to a slope angle of the inner peripheral surface of the first throttle portion 15u relative to the upstream wall surface 22a and the second angle δd is equal to a slope angle of the inner peripheral surface of the second throttle portion 15d relative to the downstream wall surface 22b.

The intake air flowing into a position upstream of the support portion 13 in the sub-bypass passage 9 is divided into two parts that are a first intake air flowing into the first region 21a and a second intake air flowing into the second region 21b. Since the width of the second region 21b is greater than the width of the first region 21a, the foreign matter included in the intake air flows into the second region 21b more readily than the first region 21a. In other words, a configuration that the foreign matter is difficult to flow into the first region 21a is achieved. Thus, it can be suppressed that the sensing accuracy of the sensing surface portion 10 is deteriorated or the sensing surface portion 10 is damaged due to the foreign matter approaching or being in contact with the sensing surface portion 10.

Since the support portion 13 extends to a position upstream of the first throttle portion 15u, a width of an upstream end part of the first region 21a is equal to the first facing distance B1. The width of the upstream end part of the first region 21a is greater than that in a configuration where the first throttle portion 15u extends to a position upstream of the support portion 13. Thus, comparing the configuration where the first throttle portion 15u extends to a position upstream of the support portion 13, a flowing passage area ratio of the first region 21a to the second region 21b becomes greater, and more intake air can flow into the first region 21a. A throttle rate is a ratio of the upstream end part of the first region 21a to a downstream end part of the first region 21a. When the width of the upstream end part becomes greater, it is likely that the throttle rate becomes greater and the flow rate of the first intake air reached the downstream end part of the first region 21a becomes greater.

The flow rate of the first intake air flowing into the first region 21a is gradually increased while the first intake air is throttled between the support portion 13 and the first throttle portion 15u after the first intake air is straightened between the support portion 13 and the upstream wall surface 22a. A part of the first region 21a between the support portion 13 and the upstream wall surface 22a functions as a straightening region that straightens the first intake air, it is difficult that the disturb that is the vortex or the separation is generated in the first intake air in the first region 21a between the support portion 13 and the first throttle portion 15u. The sensing surface portion 10 senses the flow volume based on a temperature change generated according to the flow volume of the first intake air. Thus, when the temperature change is generated due to the disturb of the flow applied to the sensing surface portion 10, the sensing accuracy of the flow volume by using the sensing surface portion 10 is deteriorated.

Since the first region 21a downstream of the first end point position βu and the second end point position βd is enlarged in the second flowing direction f2, the disturb that is the vortex or the separation is readily generated in the first intake air passing through the first end point position βu and the second end point position βd in the first region 21a. When the first intake air flowing along the first throttle portion 15u passes the first end point position βu and the second end point position βd, the disturb is generated at a position immediately downstream of the first end point position βu and the second end point position βd due to a part of the first intake air flowing along the second throttle portion 15d and a part of the first intake air flowing toward the support portion 13.

Since the sensing surface portion 10 is located upstream of the first end point position βu and the second end point position βd, it is difficult that the disturb generated at a position downstream of the first end point position βu and the second end point position βd affects the first intake air between the sensing surface portion 10 and the first throttle portion 15u. Thus, it is difficult that the sensing accuracy of the sensing surface portion 10 is deteriorated due to the disturb generated in the first intake air downstream of the first end point position βu and the second end point position βd.

Recently, since a cylinder of the internal combustion engine is miniaturized in response to a reduction of a component number or a weight reduction, an interference of the intake air in the intake air channel 2 is readily reduced, and a vibration of a flowing air relative to a flowing direction is readily increased. When a vibration frequency that is a frequency of the vibration is increased, the disturb generated in the intake air in the first region 21a is increased. Then, the measuring error of the flow measuring device 1 is readily increased. According to the present embodiment, the unit of the measuring error is %. In a configuration where the sensing surface portion 10 is located in the sub-bypass passage 9 in the bypass passage 7 without being located in the passing passage 8 in the bypass passage 7, the measuring error is readily increased in a case where the disturb generated when the intake air flows from the passing passage 8 into the sub-bypass passage 9 reaches the first region 21a.

Figure 10:
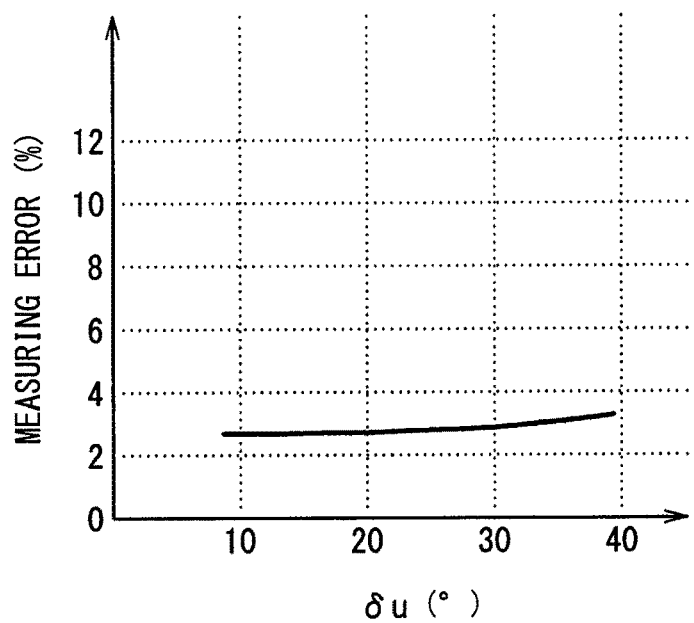
FIG. 10 is a graph showing a relationship between the measuring error and the angle in a case where the vibration frequency is a first frequency, according to the fourth embodiment.

As shown in FIG. 10, similar to the first embodiment, when the vibration frequency is a first frequency that is relatively low, the measuring error is in an allowable range in a case where the first angle δu is larger than 20 degrees. In this case, a measuring result of the flow measuring device 1 indicates a characteristic that changes in response to a change of the intake air in the intake air channel 2. As shown in FIG. 10, when the first angle δu is up to 30 degrees or 40 degrees, the measuring error is still in the allowable range. According to the present embodiment, the first frequency may be 100 Hz, and the allowable range of the measuring error may be less than or equal to 3%.

Figure 11:
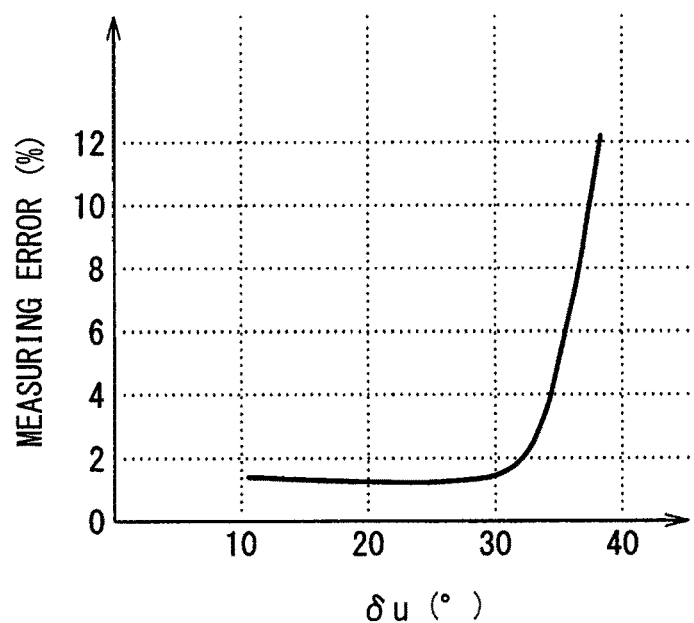
FIG. 11 is a graph showing a relationship between the measuring error and the angle in a case where the vibration frequency is a second frequency, according to the fourth embodiment.

According to the first embodiment, when the vibration frequency is a second frequency that is relative high, it is assumed that the measuring error is sharply increased to be out of the allowable range in a case where the first angle δu exceeds 20 degrees. According to the present embodiment, as shown in FIG. 11, the measuring error is still in the allowable range in a case where the first angle δu exceeds 20 degrees and is up to a value slightly exceeding 30 degrees, and the measuring error is sharply increased to be out of the allowable range in a case where the first angle δu exceeds the value slightly exceeding 30 degrees. In this case, it is difficult that the disturb is generated in the first intake air in the first region 21a in a case where the support portion 13 faces the upstream wall surface 22a in the first region 21a and the sensing surface portion 10 is located upstream of the first end point position βu and the second end point position βd.

According to the present embodiment, since the first angle δu and the second angle δd are set to 30 degrees by the first throttle portion 15u and the second throttle portion 15d, the measuring error of the flow measuring device 1 can be reduced more than that in a case where the first angle δu and the second angle δd are set to be larger than 30 degrees.

According to the present embodiment, since the sensing surface portion 10 is located between the first start point position αu and the first end point position βu, it is difficult that the disturb generated in the flow downstream of the first end point position βu is applied to the sensing surface portion 10. Thus, it can be suppressed that the sensing accuracy of the sensing surface portion 10 is deteriorated due to the disturb generated in the flow downstream of the first end point position βu. Further, since the sensing surface portion 10 is located at a position be close to the first end point position βu and the second end point position βd where the flow rate of the first intake air is readily increased in the first region 21a, the flow rate of the first intake air applied to the sensing surface portion 10 is readily increased. Thus, the sensing accuracy of the sensing surface portion 10 can be improved.

According to the present embodiment, the support portion 13 extends to a position upstream of the first start point position αu. Thus, the first intake air flowing into the first region 21a flows between the support portion 13 and the upstream wall surface 22a to be straightened before the first intake air reaches the first throttle portion 15u. Thus, it is difficult that the disturb is generated in the first intake air reaches the sensing surface portion 10.

According to the present embodiment, the gap distance B3 is shorter than the throttle distance B4. In this case, since the flow rate of the first intake air reached the first end point position βu and the second end point position βd in the first region 21a is increased more readily than the flow rate of the first intake air passing the first start point position αu, the sensing accuracy of the sensing surface portion 10 can be improved.

According to the present embodiment, the first facing distance B1 is shorter than the second facing distance B2. In this case, since the width of the first region 21a is smaller than the width of the second region 21b, a probability that the foreign matter enters the first region 21a can be reduced. Thus, it can be suppressed that the sensing accuracy of the sensing surface portion 10 is deteriorated or the sensing surface portion 10 is damaged due to the foreign matter.

Fifth Embodiment

Figure 12:
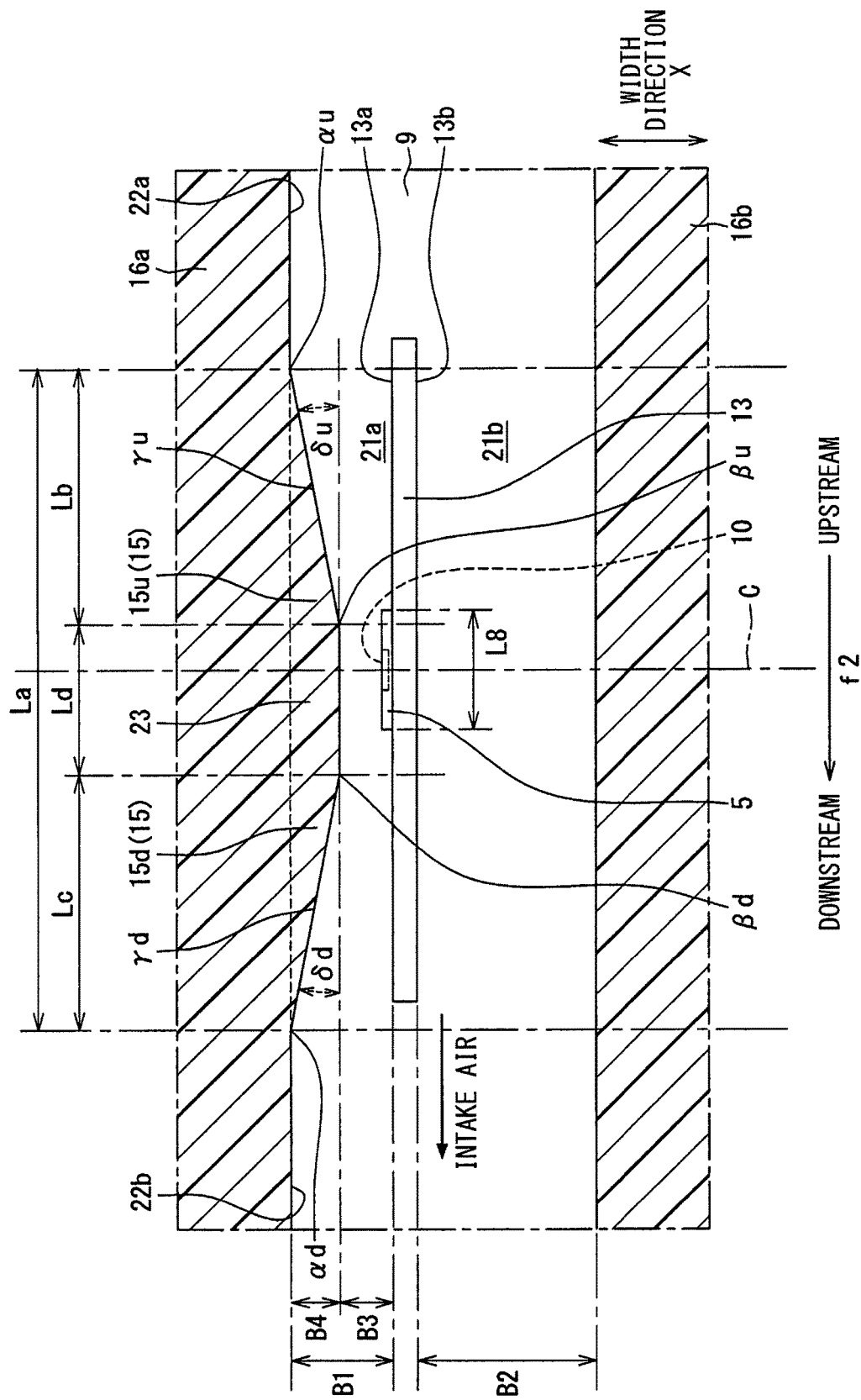
FIG. 12 is a cross-sectional view showing the flow measuring device according to a fifth embodiment of the present disclosure and corresponding to FIG. 3 in the first embodiment.

According to the fourth embodiment, the first end point position βu matches the second end point position βd. According to a fifth embodiment of the present disclosure, as shown in FIG. 12, the first end point position βu and the second end point position βd are separated from each other in the direction parallel to the second flowing direction f2. According to the present embodiment, components of the flow measuring device 1 that are different from that according to the fourth embodiment will be described.

According to the present embodiment, a connection portion 23 that is connected with the first throttle portion 15u and the second throttle portion 15d is located between the first throttle portion 15u and the second throttle portion 15d. The connection portion 23 includes an inner peripheral surface extending in a direction parallel to the upstream wall surface 22a and the downstream wall surface 22b. The connection portion 23 has a connection length Ld that is a length of the connection portion in the direction parallel to the second flowing direction f2. The connection length Ld is also a distance from the first end point position βu to the second end point position βd.

The sensing surface portion 10 is located to face the connection portion 23. Specifically, the sensing surface portion 10 is located between the first end point position βu and the second end point position βd in the direction parallel to the second flowing direction f2. The connection length Ld is longer than a chip length L8 that is a length of the flow sensing chip 5 in the direction parallel to the second flowing direction f2. The sensing surface portion 10 is located at a position close to the first end point position βu such that the flow sensing chip 5 extends to a position upstream of the first end point position βu in the second flowing direction f2. The connection portion 23 includes an upstream end located upstream of the first end point position βu and a downstream end located downstream of the second end point position βd.

According to the present embodiment, the gap distance B3 is equal to the throttle distance B4. However, the gap distance B3 may be longer than the throttle distance B4. In this case, since the width of the first region 21a in the width direction X gradually decreases in accordance with a decrease in distance between a position of the first opposite surface 13a at a cross-sectional area including the width and the gravity center of the sensing surface portion 10 in the direction parallel to the second flowing direction f2, the flow rate of the first intake air flowing between the connection portion 23 and the support portion 13 can be properly increased.

According to the present embodiment, a space of the first region 21a between the connection portion 23 and the support portion 13 is referred to as a most-throttled region. Since the sensing surface portion 10 is located in the most-throttled region, the flow rate of the first intake air applied to the sensing surface portion 10 can be sufficiently increased. Further, since the sensing surface portion 10 is located upstream of the second end point position βd as the same as that according to the fourth embodiment, it is difficult that the disturb such as the vortex generated in the flow when the intake air passes through the second end point position βd. Thus, it can be suppressed that the sensing accuracy of the sensing surface portion 10 is deteriorated due to the disturb of the flow generated downstream of the second end point position βd.

Other Embodiment

Figure 13:
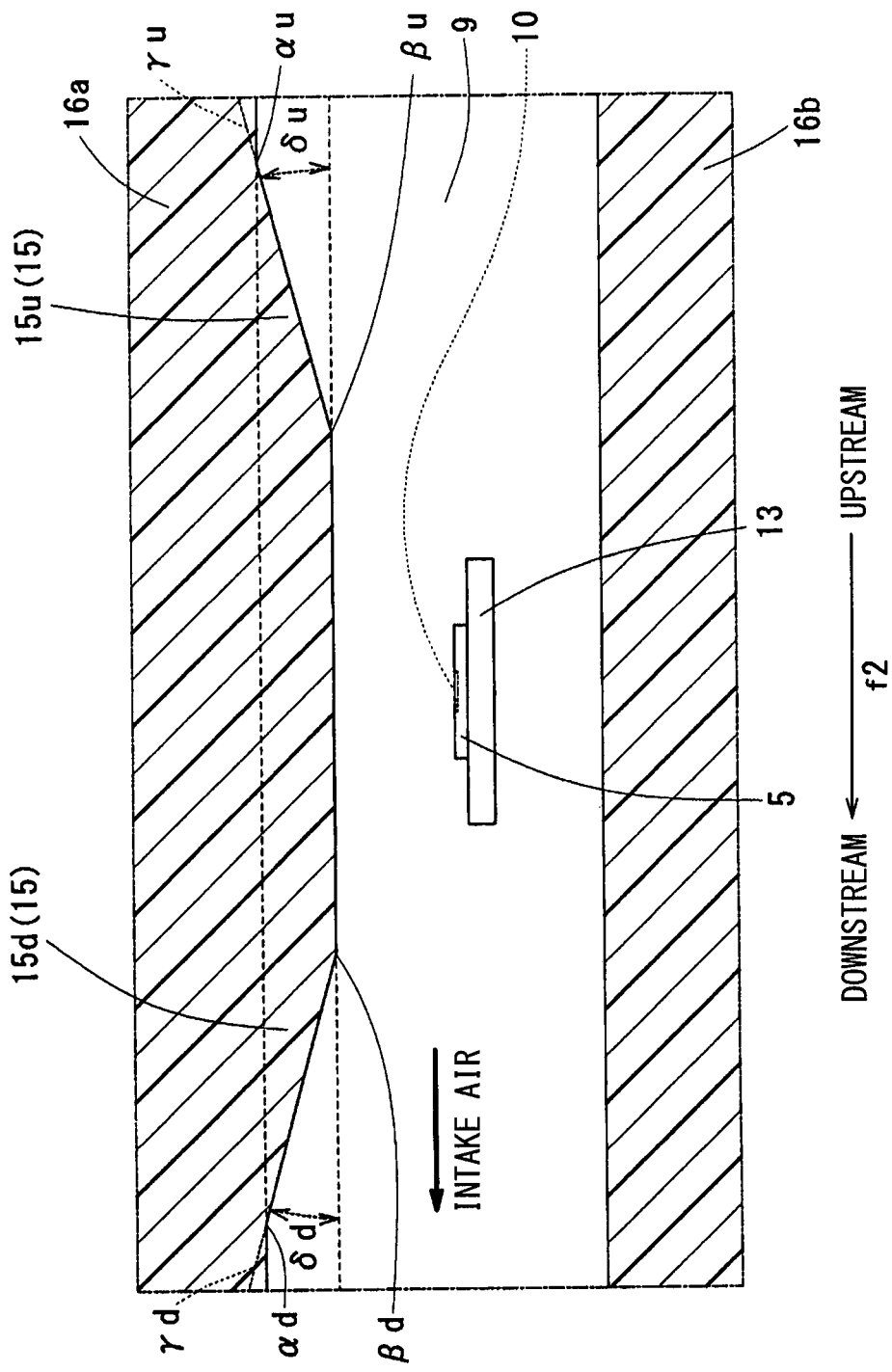
FIG. 13 is a cross-sectional view showing the flow measuring device according to a modification example of the present disclosure and corresponding to FIG. 3 in the first embodiment.

The above embodiments can be change to various embodiments within the spirit and scope of the present disclosure. According to the first embodiment, the first throttle portion 15u and the second throttle portion 15d have surfaces that are curved surfaces. As shown in FIG. 13, according to a sixth embodiment of the present disclosure that is a modification of the first embodiment, the first throttle portion 15u and the second throttle portion 15d have surfaces that are planar surfaces.

A space of the sub-bypass passage 9 between the first throttle portion 15u and the second throttle portion 15d in the direction parallel to the second flowing direction f2 is a constant region where the cross-sectional area of the sub-bypass passage 9 perpendicular to the second flowing direction f2 is minimum and is constant. The sensing surface portion 10 is located in the constant region.

Figure 14:
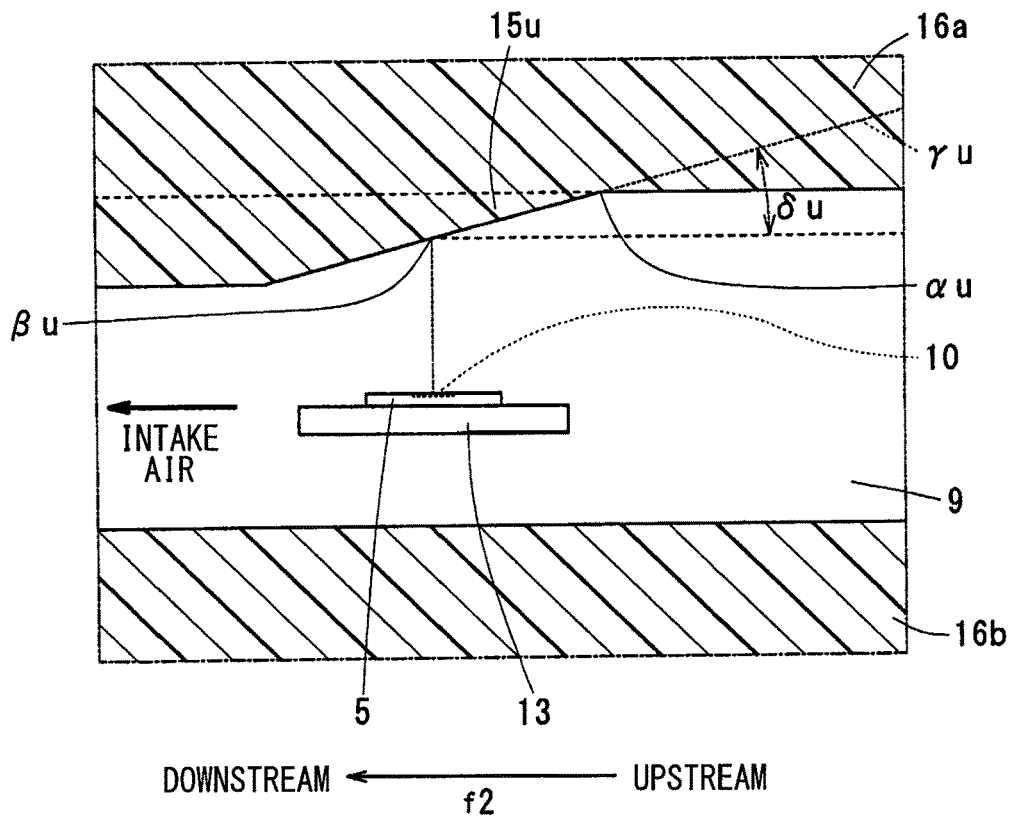
FIG. 14 is a cross-sectional view showing the flow measuring device according to another modification example of the present disclosure and corresponding to FIG. 3 in the first embodiment.

According to the second embodiment, the cross-sectional area of the sub-bypass passage 9 perpendicular to the second flowing direction f2 becomes minimum at the sensing surface portion 10. As shown in FIG. 14, according to a seventh embodiment of the present disclosure that is a modification of the second embodiment, the cross-sectional area of the sub-bypass passage 9 perpendicular to the second flowing direction f2 is minimum at a position downstream of the sensing surface portion 10.

Figure 15:
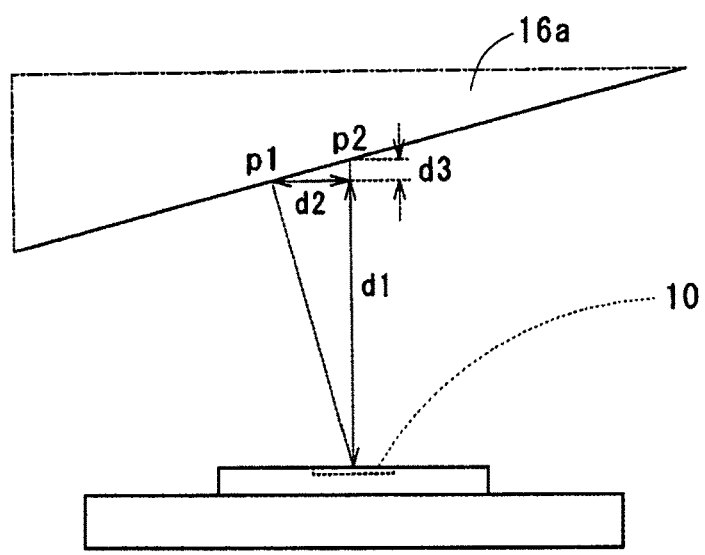
FIG. 15 is a diagram showing an end point position, according to another modification example of the present disclosure.

A distance between the first position p1 and the sensing surface portion 10 is a sum of the first distance d1 and the second distance d2 (d1+d2). A first distance d1 is a distance between the first position p1 and the sensing surface portion 10 in a direction perpendicular to the surface of the sensing surface portion 10 and the second flowing direction f2. A second distance d2 is a distance between the first position p1 and the sensing surface portion 10 in the direction parallel to the second flowing direction f2. A third distance d3 is a distance obtained by subtracting the first distance d1 from a distance between the second position p2 and the sensing surface portion 10 in the direction perpendicular to the surface of the sensing surface portion 10 and the second flowing direction f2. As shown in FIG. 15, a length of the second line L2 is equal to the distance between the second position p2 and the sensing surface portion 10 in the direction perpendicular to the surface of the sensing surface portion 10 and the second flowing direction f2. Thus, a distance between the second position p2 and the sensing surface portion 10 is equal to a sum of the first distance d1 and the third distance d3 (d1+d3). Since the first angle δu is in a range from 0 degrees to 20 degrees, the second distance d2 is longer than the third distance d3. Then, the distance between the first position p1 and the sensing surface portion 10 is longer than the distance between the second position p2 and the sensing surface portion 10. Thus, the first end point position βu is set to be located at the second position p2 that is also shown in FIG. 14. As shown in FIG. 15, a first position p1 is a position of the surface of the first flowing passage wall 16a, and the first position p1 and the gravity center of the sensing surface portion 10 define a first line L1 perpendicular to the surface of the first flowing passage wall 16a. A second position p2 is a position of the surface of the first flowing passage wall 16a, and the second position p2 and the gravity center of the sensing surface portion 10 define a second line L2 perpendicular to the surface of the sensing surface portion 10.

Figure 16:
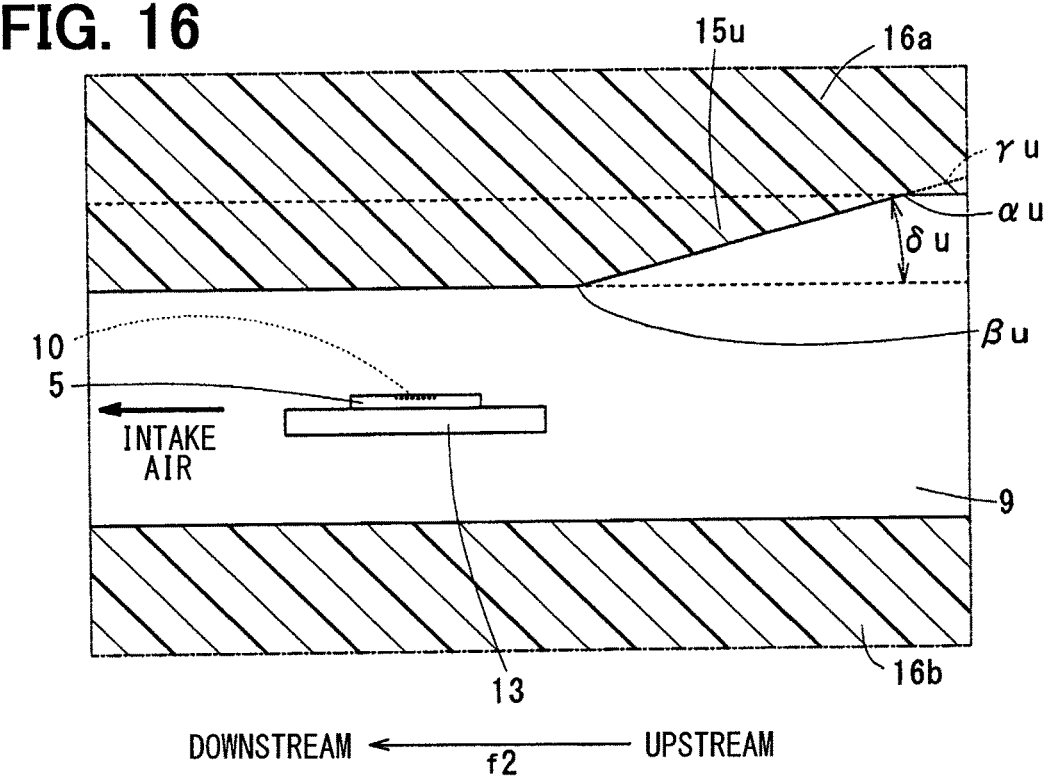
FIG. 16 is a cross-sectional view showing the flow measuring device according to another modification example of the present disclosure and corresponding to FIG. 3 in the first embodiment.

According to an eighth embodiment of the present disclosure that is another modification of the second embodiment, as shown in FIGS. 13 and 16, the first throttle portion 15u is located upstream of the sensing surface portion 10 in the second flowing direction f2.

Figure 17:
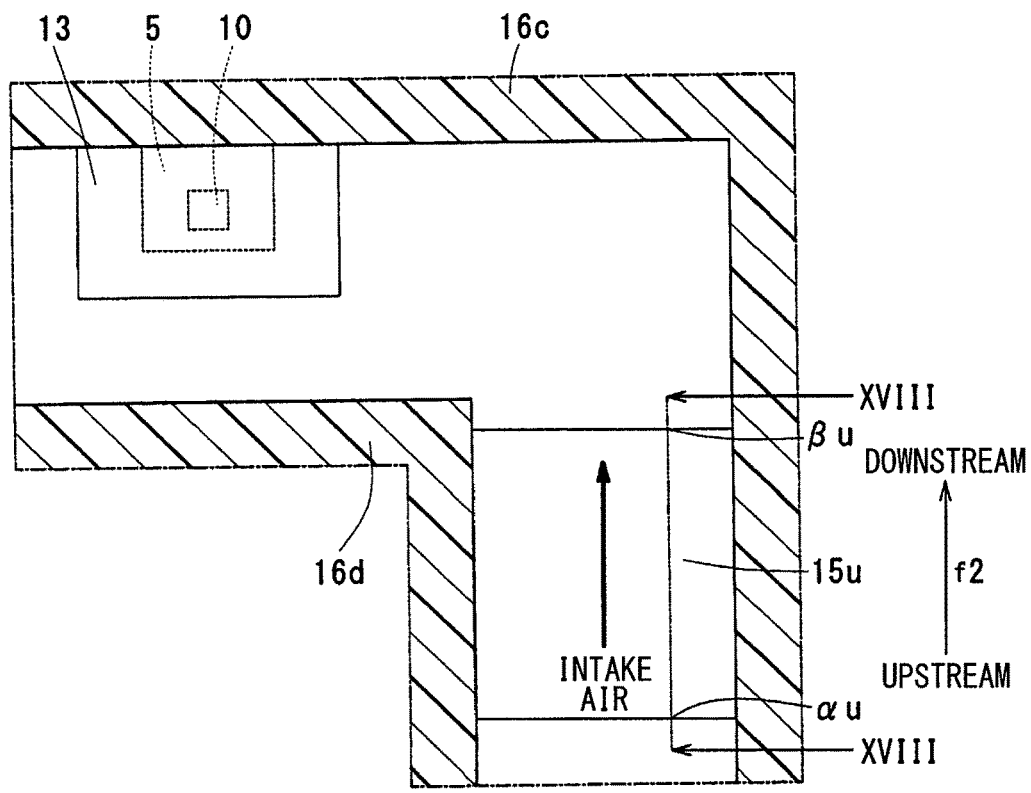
FIG. 17 is a diagram showing the flow measuring device along the flowing direction of the intake air, according to another modification example of the present disclosure.
Figure 18:
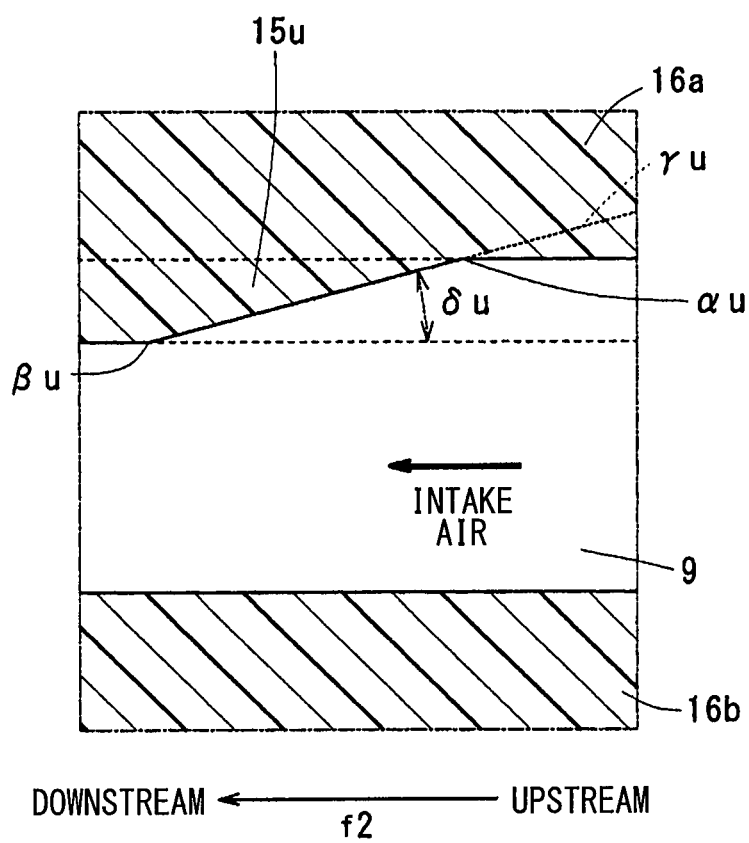
FIG. 18 is a cross-sectional view showing the flow measuring device and taken along a XVIII-XVIII line in FIG. 17.

According to a ninth embodiment of the present disclosure that is another modification of the second embodiment, as shown in FIGS. 17 and 18, the first throttle portion 15u is located at a position non-coaxial with the sensing surface portion 10 in the direction parallel to the second flowing direction f2. A distance between the sensing surface portion 10 and the first throttle portion 15u is the distance between the gravity center of the sensing surface portion 10 and the first throttle portion 15u. According to the present embodiment, at the position where the distance between the first throttle portion 15u and the gravity center of the sensing surface portion 10 is shortest, a total distance that is a sum of a distance between the gravity center of the sensing surface portion 10 and the first flowing passage wall 16a at the first throttle portion 15u in the direction perpendicular to the sensing surface portion 10 and a distance between the gravity center of the sensing surface portion 10 and the first flowing passage wall 16a at the first throttle portion 15u in the direction parallel to the second flowing direction f2 becomes shortest. In this case, the total distance is equivalent to the shortest distance between the gravity center of the sensing surface portion 10 and the first throttle portion 15u.

When plural start point positions αu exist, the first start point position αu is a position where a distance between the first start point position αu and the first end point position βu is shortest. In this case, the distance is referred to as a shortest distance between the first start point position αu and the first end point position βu. According to the present embodiment, at the position where the distance between the first start point position αu and the first end point position βu is shortest, a total distance that is a sum of a distance between the first start point position αu and the first end point position βu in the direction perpendicular to the sensing surface portion 10 and a distance between the first start point position αu and the first end point position βu in the direction parallel to the second flowing direction f2 becomes shortest. In this case, the total distance is equivalent to the shortest distance between the first start point position αu and the first end point position βu.

According to the third embodiment, the second throttle portion 20 is located on the second flowing passage wall 16b facing the first flowing passage wall 16a. According to a tenth embodiment of the present disclosure that is a modification of the third embodiment, the second throttle portion 20 is located on a flowing passage wall other than the second flowing passage wall 16b. Since the vortex slightly affects the sensing surface portion 10 when a flowing passage wall is separated from the sensing surface portion 10 by a predetermined distance, the second throttle portion 20 can be located on the first flowing passage wall 16a.

According to the first embodiment, the second embodiment and the third embodiment, the housing 3 includes the sub-bypass passage 9 that is a part of the bypass passage 7. According to an eleventh embodiment of the present disclosure that is a modification of the first embodiment, the second embodiment and the third embodiment, the housing 3 excludes the sub-bypass passage 9.

According to a twelfth embodiment of the present disclosure that is a modification of the fourth embodiment and the fifth embodiment, the first angle δu and the second angle δd are smaller than 30 degrees. When the first angle δu and the second angle δd are in a range from 0 degrees to 30 degrees, a configuration where the measuring error is not sharply increased until the first angle δu exceeds 30 degrees can be achieved, as shown in FIG. 11. Further, similarly, a configuration where the measuring error is not sharply increased until the second angle δd exceeds 30 degrees can be achieved.

According to a thirteenth embodiment of the present disclosure that is another modification of the fourth embodiment and the fifth embodiment, the support length L1 is different from the throttle length La. In a configuration where the support length L1 is longer than the throttle length La, the support portion 13 extends to a position upstream of the first throttle portion 15u and extends to a position downstream of the second throttle portion 15d in the second flowing direction f2. In a configuration where the support length L1 is shorter than the throttle length La, the support portion 13 extends to a position upstream of the first throttle portion 15u.

According to a fourteenth embodiment of the present disclosure that is another modification of the fourth embodiment and the fifth embodiment, the flow sensing chip 5 and the sensing surface portion 10 is located at a position upstream or downstream of a center position of the support portion 13 in the second flowing direction f2. Further, the sensing surface portion 10 is located at a position upstream or downstream of a center position of the flow sensing chip 5 in the second flowing direction f2.

According to a fifteenth embodiment of the present disclosure that is another modification of the fourth embodiment, an entire of the flow sensing chip 5 is located upstream of the first end point position βu and the second end point position βd. In this case, the sensing surface portion 10 can be located at a position close to the first end point position βu and the second end point position βd in the direction parallel to the second flowing direction f2.

According to a sixteenth embodiment of the present disclosure that is another modification of the fifth embodiment, at least a part of the sensing surface portion 10 is located upstream of the first end point position βu. For example, an entire of the sensing surface portion 10 is located upstream of the first end point position βu. In this case, the sensing surface portion 10 does not face the connection portion 23, and the sensing surface portion 10 faces the first throttle portion 15u as the same as that according to the fourth embodiment.

According to a seventeenth embodiment of the present disclosure that is another modification of the fourth embodiment and the fifth embodiment, the first angle δu and the second angle δd are smaller than 30 degrees. For example, the first angle δu is smaller than the second angle δd, or the first angle δu is bigger than the second angle δd. In this case, since a configuration where the measuring error is not sharply increased until the first angle δu exceeds 30 degrees can be achieved as shown in FIG. 11, the sensing accuracy of the sensing surface portion 10 and a measuring accuracy of the flow measuring device 1 can be properly maintained. Further, similarly, since a configuration where the measuring error is not sharply increased until the second angle δd exceeds 30 degrees can be achieved, the sensing accuracy of the sensing surface portion 10 and the measuring accuracy of the flow measuring device 1 can be properly maintained.

According to an eighteenth embodiment of the present disclosure that is another modification of the fourth embodiment and the fifth embodiment, the support portion 13 is not located upstream of the first start point position αu. In this case, when the support portion 13 is located at a position where the first flowing passage wall 16a is closer to the support portion 13 than other flowing passage walls are in the width direction X, the measuring error is not sharply increased until the first angle δu or the second angle δd exceeds 30 degrees. In a configuration where the support portion 13 is located at a position where the first flowing passage wall 16a is closer to the support portion 13 than other flowing passage walls are in the width direction X, the first facing distance B1 is shorter than the second facing distance B2.

According to a nineteenth embodiment of the present disclosure that is another modification of the fourth embodiment and the fifth embodiment, the support portion 13 is not located at a position where the first flowing passage wall 16a is closer to the support portion 13 than other flowing passage walls are in the width direction X. In this case, when the support portion 13 is located upstream of the first start point position αu in the second flowing direction f2, the measuring error is not sharply increased until the first angle δu or the second angle δd exceeds 30 degrees.

According to an aspect of the present disclosure, the flow measuring device includes a housing including a bypass passage that introduces a part of an air flowing through a duct, and a flow sensing chip located in the bypass passage and including a sensing portion that generates an electrical signal in response to a flow volume of the air in the duct. The bypass passage is throttled by a throttle portion such that a cross-sectional area of the bypass passage perpendicular to a flowing direction in which the air flows through the bypass passage decreases in accordance with a decrease in distance from a gravity center of the sensing surface portion to a center of the cross-sectional area in a direction parallel to the flowing direction. The throttle portion is a part of a flowing passage wall facing the sensing surface portion. A position where the throttle portion starts is referred to as a start point position, the start point position is located upstream of the sensing portion in the flowing direction. The throttle portion includes a surface that is a planar surface, the surface of the throttle portion and the flowing direction define an angle that is in a range from 0 degrees to 30 degrees.

According to another aspect of the present disclosure, the flow measuring device measures a flow volume of an air. The flow measuring device includes a bypass passage through which the air flows, a sensing portion outputting an electrical signal in response to the flow volume of the air in the bypass passage, a pair of flowing passage walls facing each other, the sensing portion located between the flowing passage walls, and a throttle portion throttling the bypass passage by protruding from the flowing passage walls toward the sensing portion, in an arrangement direction in which the pair of the flowing passage walls is arranged. The throttle portion has a protruding dimension gradually increases in accordance with a decrease in distance from the throttle portion to the sensing portion from an upstream end of the throttle portion in the bypass passage in a flowing direction in which the air flows through the bypass passage. A position of an upstream end of the throttle portion is referred to as a start point position, and a position of the throttle portion where a distance between the gravity center of the sensing surface portion and the throttle portion is shortest is referred to as an end point position. The start point position and the end point position define an imagination line, and the imagination line and the flowing direction define an angle that is in a range from 0 degrees to 30 degrees.

While the present disclosure has been described with reference to the embodiments thereof, it is to be understood that the disclosure is not limited to the embodiments and constructions. The present disclosure is intended to cover various modification and equivalent arrangements. In addition, while the various combinations and configurations, which are preferred, other combinations and configurations, including more, less or only a single element, are also within the spirit and scope of the present disclosure.

What is claimed is:

1. A flow measuring device comprising:
   a housing including a bypass passage that introduces a part of an air flowing through a duct; and
   a flow sensing chip located in the bypass passage and including a sensing surface portion that generates an electrical signal in response to a flow volume of the air in the duct by a heat transmission between the sensing surface portion and the air flowing through the bypass passage, wherein
   the sensing surface portion is located along a flowing direction in which the air flows through the bypass passage,
   the bypass passage is throttled by a throttle portion such that a cross-sectional area of the bypass passage perpendicular to the flowing direction decreases in accordance with a decrease in distance from a gravity center of the sensing surface portion to a center of the cross-sectional area in a direction parallel to the flowing direction,
   the throttle portion is a part of a flowing passage wall facing the sensing surface portion, the throttle portion throttles the cross-sectional area of the bypass passage such that a distance from the sensing surface portion to the flowing passage wall at the cross-sectional area in a direction perpendicular to the sensing surface portion decreases in accordance with a decrease in distance from the gravity center of the sensing surface portion to the center of the cross-sectional area in the direction parallel to the flowing direction,
   a position where the throttle portion starts is referred to as a start point position, and a position of the throttle portion where a distance between the gravity center of the sensing surface portion and the throttle portion is shortest is referred to as an end point position, and
   the start point position and the end point position define an imagination line, and the imagination line and the flowing direction define an angle that is in a range from 0 degrees to 20 degrees.

2. The flow measuring device according to claim 1, wherein
   the throttle portion includes a surface that is a planar surface or a curved surface.

3. The flow measuring device according to claim 1, wherein
   another throttle portion that is different from the throttle portion is located in the bypass passage.

4. The flow measuring device according to claim 1, wherein
   the throttle portion extends in the direction parallel to the flowing direction, the throttle portion includes a first part located upstream of the gravity center of the sensing surface portion in the flowing direction and a second part located downstream of the gravity center of the sensing surface portion in the flowing direction.

5. The flow measuring device according to claim 1, wherein
   the bypass passage is configured to introduce the part of the air flowing through the duct along a main-flow direction; and
   the housing defines an outlet that discharges the air that passed through the sensing surface portion into the duct from the bypass passage, and
   the outlet opens along the main-flow direction.

6. A flow measuring device comprising:
   a housing including a bypass passage that introduces a part of an air flowing through a duct; and
   a flow sensing chip located in the bypass passage and including a sensing surface portion that generates an electrical signal in response to a flow volume of the air in the duct, wherein
   the bypass passage is throttled by a throttle portion such that a cross-sectional area of the bypass passage perpendicular to a flowing direction in which the air flows through the bypass passage decreases in accordance with a decrease in distance from a gravity center of the sensing surface portion to a center of the cross-sectional area in a direction parallel to the flowing direction,
   the throttle portion is a part of a flowing passage wall facing the sensing surface portion,
   a position where the throttle portion starts is referred to as a start point position, the start point position is located upstream of the sensing surface portion in the flowing direction, and
   the throttle portion includes a surface that is a planar surface, the surface of the throttle portion and the flowing direction define an angle that is in a range from 0 degrees to 20 degrees.

7. A flow measuring device comprising:
   a housing including a bypass passage that introduces a part of an air flowing through a duct along a main-flow direction; and
   a flow sensing chip located in the bypass passage and including a sensing surface portion that generates an electrical signal in response to a flow volume of the air in the duct by a heat transmission between the sensing surface portion and the air flowing through the bypass passage, wherein the sensing surface portion is located along a flowing direction in which the air flows through the bypass passage, the bypass passage is throttled by a throttle portion such that a cross-sectional area of the bypass passage perpendicular to the flowing direction decreases in accordance with a decrease in distance from a gravity center of the sensing surface portion to a center of the cross-sectional area in a direction parallel to the flowing direction, the throttle portion is a part of a flowing passage wall that is included in the housing and faces the sensing surface portion, the throttle portion throttles the cross-sectional area of the bypass passage such that a distance from the sensing surface portion to the flowing passage wall at the cross-sectional area in a direction perpendicular to the sensing surface portion decreases in accordance with a decrease in distance from the gravity center of the sensing surface portion to the center of the cross-sectional area in the direction parallel to the flowing direction, a position where the throttle portion starts is referred to as a start point position, and a position of the throttle portion where a distance between the gravity center of the sensing surface portion and the throttle portion is shortest is referred to as an end point position, the start point position and the end point position define an imagination line, and the imagination line and the flowing direction define an angle that is in a range from 0 degrees to 30 degrees, the housing defines an outlet that discharges the air that passed through the sensing surface portion into the duct from the bypass passage, and the outlet opens along the main-flow direction.

8. The flow measuring device according to claim 7, wherein a distance from the end point position to a support portion supporting the sensing surface portion is shorter than a distance from the start point position to the end point position, in an orthogonal direction perpendicular to the flowing direction.

9. The flow measuring device according to claim 7, wherein the flowing passage wall is a first flowing passage wall, the housing includes a second flowing passage wall facing the first flowing passage wall, a support portion supporting the sensing surface portion is located between the first flowing passage wall and the second flowing passage wall, the sensing surface portion is located on a surface of the support portion facing the first flowing passage wall, a distance from the start point position of the first flowing passage wall to the support portion is shorter than a distance from the support portion to the second flowing passage wall.

10. The flow measuring device according to claim 7, wherein the throttle portion is an upstream throttle portion that is located at a position in the bypass passage upstream of the sensing surface portion and extends in the flowing direction to throttle the bypass passage, and the sensing surface portion includes a center part that is located between the start point position and the end point position in the flowing direction.

11. The flow measuring device according to claim 10, further comprising:

a support portion being a plate shape, the support portion supporting the sensing surface portion, the support portion extending to a position upstream of the throttle portion.

* * * * *